United States Patent
Uehata et al.

(12)

(10) Patent No.: US 6,218,410 B1
(45) Date of Patent: Apr. 17, 2001

(54) MEDICINES COMPRISING RHO KINASE INHIBITOR

(75) Inventors: Masayoshi Uehata; Takashi Ono, both of Iruma; Hiroyuki Satoh, Chikujo-gun; Keiji Yamagami, Iruma; Toshio Kawahara, Chikujo-gun, all of (JP)

(73) Assignee: Yoshitomi Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/242,261

(22) PCT Filed: Aug. 8, 1997

(86) PCT No.: PCT/JP97/02793

§ 371 Date: Apr. 16, 1999

§ 102(e) Date: Apr. 16, 1999

(87) PCT Pub. No.: WO98/06433

PCT Pub. Date: Feb. 19, 1998

(30) Foreign Application Priority Data

Aug. 12, 1996 (JP) .................................................. 8-212409

(51) Int. Cl.$^7$ ........................ A61K 31/445; A61K 31/44; A61K 31/495; A61K 31/195

(52) U.S. Cl. .......................... 514/352; 514/241; 514/242; 514/243; 514/245; 514/246; 514/256; 514/258; 514/275; 514/300; 514/303

(58) Field of Search ............................ 546/309; 514/352, 514/241, 242, 243, 245, 246, 256, 258, 275, 300, 303

(56) References Cited

U.S. PATENT DOCUMENTS 5,478,838   12/1995   Arita et al. ........................... 514/300

FOREIGN PATENT DOCUMENTS

| 0 757 038 A1 | 2/1997 | (EP) . |
|---|---|---|
| 62-89679 | 4/1987 | (JP) . |
| 3-218356 | 9/1991 | (JP) . |
| 4-273821 | 9/1992 | (JP) . |
| 5-194401 | 8/1993 | (JP) . |

OTHER PUBLICATIONS

CPI English Abstract AN82–86109E/41 of EP–61673–A (corresponding patent of JP, 57–200366, A).
CPI English Abstract AN86–184348/29 of EP–187371–A (corresponding patent of JP, 61–227581, A).
CPI English Abstract AN90–357445/48 of JP, 2–256617, A.
CPI English Abstract AN92–361902/44 of JP, 2–264030, A.
CPI English Abstract AN94–065376/08 of WO94/03171 (corresponding patent of JP, 6–56668, A).
CPI English Abstract AN94–100832/12 of WO94/05290 (corresponding patent of JP, 6–80569, A).
CPI English abstract AN95–009548/02 of JP, 6–293643, A.
CPI English abstract AN95–118658/16 of JP, 7–41424, A.
CPI English abstract AN96–003284/01 of JP, 7–277979, A.

Primary Examiner—Zinna Northington Davis
(74) Attorney, Agent, or Firm—Wenderoth, Lind & Ponack, L.L.P.

(57) ABSTRACT

A Rho kinase inhibitor is provided as a novel pharmaceutical agent, particularly as a therapeutic agent of hypertension, a therapeutic agent of angina pectoris, a suppressive agent of cerebrovascular contraction, a therapeutic agent of asthma, a therapeutic agent of peripheral circulation disorder, a prophylactic agent of immature birth, a therapeutic agent of arteriosclerosis, an anti-cancer drug, an anti-inflammatory agent, an immunosuppressant, a therapeutic agent of autoimmune disease, an anti-AIDS drug, a contraceptive, a prophylactic agent of digestive tract infection, a therapeutic agent of osteoporosis, a therapeutic agent of retinopathy and a brain function improving drug. In addition, the Rho kinase inhibitor is provided as a reagent and a diagnostic.

18 Claims, No Drawings

MEDICINES COMPRISING RHO KINASE INHIBITOR

This application is a 371 of PCT/JP97/02793 filed Aug. 8, 1997.

TECHNICAL FIELD

The present invention relates to treatment of various diseases by the use of a Rho kinase inhibitor as a pharmaceutical agent. Moreover, the present invention relates to use of a Rho kinase inhibitor as a reagent or a diagnostic.

BACKGROUND ART

Ever since the discovery of Ras in 1981, a number of small GTP binding proteins (small G proteins) similar to Ras have been found, and many physiological functions they possess have been studied. These small G proteins have a molecular weight of 20,000–30,000 and do not have a subunit structure. They all specifically bind GDP and GTP, and hydrolyze the thus-bound GTP (GTPase activity) (Hall, A., Science, 249, 635–640, 1990; Bourne, H. R. et al., Nature, 349, 117–127, 1991).

To date, more than 50 kinds of genes encoding these small G proteins have been found from yeast to mammals, forming a superfamily. These small G proteins are largely divided into 5 groups of Ras, Rho, Rab, Arf and others, according to the similarity of amino acid sequences.

Of these, Rho was named so because its gene isolated in the form of cDNA from sea hare neuromuscle encodes a polypeptide having about 35% homology with Ras (Ras homologue) (Madaule, P., Cell, 41, 31–40, 1985).

Rho is specifically ADP ribosylated by C3 enzyme, which is one of the botulinum toxins, and Staphylococcal toxin EDIN, and inactivated (Narumiya, S. and Morii, S., Cell Signal, 5, 9–19, 1993; Sekine, A. et al., J. Biol. Chem., 264, 8602–8605, 1989). Hence, the C3 enme and EDIN were used to study the involvement of Rho in cell functions from various aspects.

For example, phosphorylation by myosin light chain (MLC) kinase is considered to enable actin * myosin interaction and initiate contraction of smooth muscle, and the structure of smooth muscle myosin phosphatase which dephosphorylates MLC has been clarified (Shimizu, H. et al., J. Biol. Chem., 269, 30407–30411, 1994). It has been clarified that the activity of myosin phosphatase is, like MLC kinase, under the control of the intracellular signal transduction system and Rho is involved in this mechanism. Moreover, an active Rho bound with GTP has been found to enhance Ca-dependent contraction in a smooth muscle skinned fiber specimen (Hirata, K., J. Biol. Chem., 267, 8719–8722, 1992), thereby suggesting that the increase in Ca sensitivity in smooth muscle contraction is caused by the inhibition of myosin phosphatase activity via Rho.

In Swiss 3T3 cell and 3Y 1 cell, moreover, Rho-dependent promotion of tyrosine phosphorylation (Kumagai, N. et al., J. Biol. Chem., 270, 8466–8473, 1993) and activation of many kinds of serine/threonine kinases (Kumagai, N. et al., FEBS Lett., 366, 11–16, 1995) have been acknowledged. From this, the presence of plural protein kinases in the downstream of Rho in the signal transduction pathway via Rho has been suggested and, actually, ROCα (Leung, T. et al., J. Biol. Chem., 270,29051–29054, 1995) [another name Rho-kinase, ROCK-II] and p160ROCK (Ishizaki, T. et al., The EMBO J., 15(8), 1885–1893, 1996) [another name ROCβ, ROCK-I] have been reported as serine/threonine kinase (Rho kinase) activated along with the activation of Rho. It has been also reported that biological distribution of the both enzymes is different (Nakagawa, O. et al., FEBS Lett. 392 189–193, 1996). In addition, it has been reported that this Rho kinase directly phosphorylates myosin phosphatase and inhibits its activity (Kimura, K. et al., Science, 273, 245–248, 1996).

Rho has been documented to be responsible for the activation of not only protein kinase but also lipid kinase (Zang, J. et al., J. Biol. Chem., 268, 22251–22254, 1993), and the presence of phospholipase (PLD) activated by Rho has been also suggested (Siddiqi, A. R. et al., J. Biol. Chem., 268, 24535–24538, 1995).

Control by Rho of the motility of Swiss 3T3 fibroblasts in the presence of serum, motility of keratinocyte 303R by HGF and TPA (12-O-tetradecanoylphorbol 13-acetate), spontaneously occurred and chemoatractant mediated motility of neutrophils have been reported (Takai, Y. et al., Trends Biochem. Sci., 20,227–231, 1995), and control of the permeation of liver cancer cell (MM1 cell), which is one of the metastatic cancer models, through cultured mesothelial layer by the activation of Rho has been reported (Yoshioka, K. et al., FEBS Lett., 372, 25–28, 1995), thereby suggesting the involvement of Rho in cell motility.

Meanwhile, in the cells derived from nerves, such as neuroblastoma, PC-12 cells and the like, retraction of neurite and rounding of the cell by lysophosphatidic acid, which is an activation stimulant of Rho, have been acknowledged. Inasmuch as this retraction can be inhibited by C3 enzyme treatment (Jalink, K. et al., J. Cell Biol., 126, 801–810, 1994) and the formation of ringed structure of podosome, which separates the site where dissolution and absorption of bone take place in the clear zone of osteoclast from the surrounding, is inhibited by C3 enzyme treatment (Zhang, D. et al., J. Cell Sci., 108, 2285–2292, 1995), a deep involvement of Rho in the morphological changes in cells has been suggested.

In addition, C3 enzyme treatment reportedly inhibits activation of an adhesion molecule such as LFA (leukocyte function-associated antigen) and the like, and C3 enzyme treatment reportedly inhibits proliferation of Swiss 3T3 fibroblasts (Yamamoto, M. et al., Oncogene, 8, 1449–1455, 1993). Thus, Rho reportedly controls cell adhesion and cell division via actin cytoskeleton, and is also concerned with the transcription control of c-fos gene (Hill, C. S. et al., Cell, 81, 1159–1170, 1995) and transformation of cell (Khosravi-Far, R. et al., Mol. Cell Biol., 15(11), 6443–6453, 1995).

In view of the inhibition of invasion of dysentery bacillus into epithelial cells by C3 enzyme, a recent report has documented the deep involvement of Rho in bacterial infection (Adam, T. et al., The EMBO J., 15(13), 3315, 1996).

In pregnant rats, moreover, the levels of Rho and Rho kinase are reported to be higher as compared to nonpregnant rats (Niiro, N. et al., Biochem. Biophys. Res. Commun., 230, 356–359, 1997), and deep involvement of Rho and Rho kinase in muscle contraction of uterus for childbirth has been known. Further, integrin (Sueoka, K. et al., Fertility & Sterility, 67(5) 799–811, 1997) considered to be involved in the cell-cell and cell-extracellular matrix adhesion during the stages of fertilization, embryogenesis and embryonidation is known to be activated by Rho (Morii, N. et al., J. Biol. Chem., 267, 20921–20926, 1992).

Hence, it has been made clear that Rho is activated upon receipt of signals from various cell membrane receptors and the activated Rho functions as a molecule switch of a broad range of cell phenomena, such as smooth muscle contraction, cell motility, cell adhesion, morphological changes of cell, cell growth and the like, via actomyosin system.

Smooth muscle contraction is significantly involved in the disease states of hypertension, angina pectoris, cerebrovascular contraction, asthma, peripheral circulation disorder, imminent immature birth and the like; cell motility plays an important role in invasion and metastasis of cancer, arteriosclerosis, retinopathy, immune response and the like; cell adhesion is deeply involved in metastasis of cancer, inflammation, autoimmune disease, AIDS, fertilization and nidation of fertilized egg and the like; morphological change of cell is deeply involved in brain function disorder, osteoporosis, bacterial infection of digestive tract and the like; and cell growth is deeply involved in cancer, arteriosclerosis and the like. Therefore, a drug that blocks the functions of Rho is considered to make a therapeutic agent for these diseases in which Rho plays some role.

At present, however, only C3 enzyme and EDIN can inhibit the actions of Rho. These are proteins which cannot permeate cytoplasm, which prevents their development as a pharmaceutical agent.

On the other hand, inhibition of Rho kinase, which is considered to be present downstream of the signal transduction pathway via Rho, is considered to lead to the inhibition of responses of various cell phenomena due to Rho. However, a specific inhibitor of Rho kinase has not been known to date.

It is expected, therefore, that by searching a compound that inhibits Rho kinase, such Rho kinase inhibitor will be an effective agent for the prophylaxis and/or treatment of the above-mentioned diseases and phenomena relating to Rho, such as hypertension, angina pectoris, cerebrovascular contraction, asthma, peripheral circulation disorder, immature birth, arteriosclerosis, cancer, inflammation, immune disease, autoimmune disease, AIDS, fertilization and nidation of fertilzed egg, osteoporosis, retinopathy, brain function disorder, bacterial infection of digestive tract and the like.

The compound of the formula (I) is already known to be useful as an agent for the prophylaxis and treatment of circulatory disorder in coronary, cerebral, renal and peripheral arteries and the like (e.g., a potent and long lasting therapeutic agent of hypertension, angina pectoris, renal and peripheral circulation disorder, and suppressive agent of cerebrovascular contraction and the like), as well as a therapeutic agent of asthma (Japanese Patent Unexined Publication No. 62-89679, Japanese Patent Unexamined Publication No. 3-218356, Japanese Patent Unexamined Publication No. 4-273821, Japanese Patent Unexamined Publication No. 5-194401, Japanese Patent Unexamined Publication No. 6-41080 and WO95/28387 and the like).

The compound of the formula (II) is already known to be useful as a vasodilator, a therapeutic agent of hypertension, a brain function improving agent, an anti-asthma agent, a heart protection agent, a platelet aggregation inhibitor, a psychosyndrome treating agent, an anti-inflammatory agent and an agent for the prophylaxis and treatment of hyperviscosity syndrome (Japanese Patent Unexamined Publication No. 57-200366, Japanese Patent Unexamined Publication No. 61-227581, Japanese Patent Unexamined Publication No. 2-256617, Japanese Patent Unexamined Publication No. 4-264030, Japanese Patent Unexamined Publication No. 6-56668, Japanese Patent Unexamined Publication No.6-80569, Japanese Patent Unexamined Publication No. 6-293643, Japanese Patent Unexamined Publication No. 7-41424 and Japanese Patent Unexamined Publication No. 7-277979).

However, these compounds of the formula (I) or (II) are not known to block the functions of Rho or to have Rho kinase inhibitory action.

DISCLOSURE OF THE INVENTION

The present invention aims at providing a Rho kinase inhibitor as a novel pharmaceutical agent. As a result of intensive studies, the present inventors have found that a compound inhibiting Rho kinase has an antihypertensive action, an anti-angina pectoris action, a cerebrovascular contraction suppressive action, an anti-asthma action, a peripheral circulation improving action, an immature birth preventive action, an anti-arteriosclerosis action, an anti-cancer action, an antiinflammatory action, an immunosuppressive action, an autoimmune disease improving action, an anti-AIDS action, a preventive action on fertilization and nidation of fertilized egg, an osteoporosis treating action, a retinopathy treating action, a brain function improving action, a preventive action on bacterial infection of digestive tract and that the Rho linase inhibitor is useful as a pharmaceutical agent, particularly as a therapeutic agent of hypertension, a therapeutic agent of angina pectoris, a suppressive agent of cerebrovascular contraction, a therapeutic agent of asthma, a therapeutic agent of peripheral circulation disorder, a prophylactic agent of immature birth, a therapeutic agent of arteriosclerosis, an anti cancer drug, an anti-inflammatory agent, an immunosuppressant, a therapeutic agent of autoimmune disease, an anti-AIDS drug, a therapeutic agent of osteoporosis, a therapeutic agent of retinopathy, a brain function improving drug, a contraceptive and a prophylactic agent of digestive tract infection, which resulted in the completion of the present invention.

It has been also found that a compound which inhibits Rho kinase is useful as a reagent for the study of Rho and Rho kinase and as a diagnostic of the diseases relating to those, which resulted in the completion of the present invention.

Accordingly, the present invention provides the following.

(1) A pharmaceutical agent containing a Rho kinase inhibitor.
(2) A pharmaceutical agent containing a Rho kinase inhibitor, which is at least one member selected from the group consisting of a therapeutic agent of hypertension, a therapeutic agent of angina pectoris, a suppressive agent of cerebrovascular contraction, a therapeutic agent of asthma, a therapeutic agent of peripheral circulation disorder, a therapeutic agent of arteriosclerosis, an anti-cancer drug, an anti-inflammatory agent, an immunosuppressant, a therapeutic agent of autoimmune disease, an anti-AIDS drug, a therapeutic agent of osteoporosis, a therapeutic agent of retinopathy, a brain function improving drug, a prophylactic agent of immature birth, a contraceptive and a prophylactic agent of digestive tract infection.
(3) A pharmaceutical composition containing a therapeutically effective amount of a Rho kinase inhibitor and a pharmaceutically acceptable additive.
(4) A reagent containing a Rho kinase inhibitor.
(5) A diagnostic containing a Rho kinase inhibitor.
(6) A Rho kinase inhibitor containing an amide compound of the formula (I):

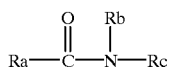

(I)

wherein

Ra is a group of the formula:

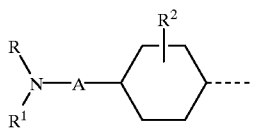

(a)

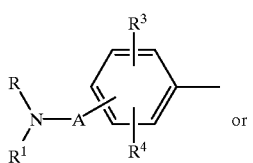

(b)

or (c)

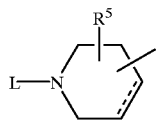

in the formulas (a) and (b),

R is hydrogen, alkyl or cycloalkyl, cycloalkylalkyl, phenyl or aralkyl, which optionally have a substituent on the ring, or a group of the formula:

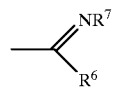

(d)

wherein $R^6$ is hydrogen, alkyl or formula: —$NR^8NR^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally having, in the ring, oxygen atom, sulfur atom or optionally substituted nitrogen atom, $R^1$ is hydrogen, alkyl or cycloalkayl, cycloalkylalkyl, phenyl or aralkyl, which optionally have a substituent on the ring, or R and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula:

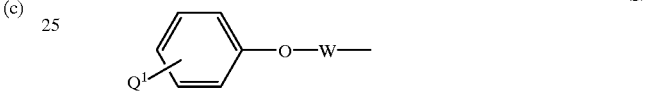

(e)

wherein $R^{10}$ and $R^{11}$ are the same or different and each is hydrogen, alkyl, haloalkyl, aralyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono or dialkylaminoalkyl, tetrahydrofurfryl, carbamoylalkyl, phthalimidoalkyl, amidino or a group of the formula:

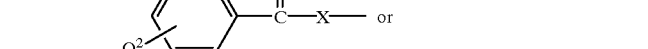

(f)

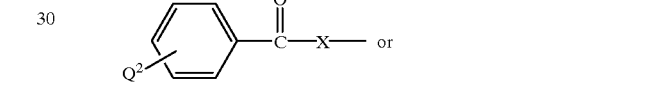

(g)

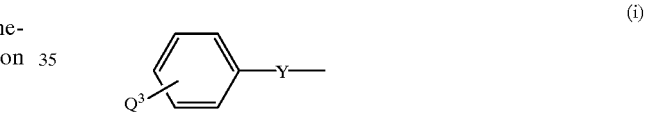

(h)

or (i)

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styrl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl;

and Y is a single bond, alkylene or alkenylene, and in the formula (c), a broken line is a single bond or a double bond, and $R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof.

(7) A pharmaceutical agent containing a compound of the formula (I), an isomer thereof and/or a pharmaceutically acceptable acid addition salt thereof, which is a therapeutic agent of at least one disease selected from the group consisting of hypertension, angina pectoris, cerebrovascular contraction, asthma and peripheral circulation disorder, which are caused by Rho kinase.

(8) A pharmaceutical agent containing a compound of the formula (I), an isomer thereof and/or a pharmaceutically acceptable acid addition salt thereof, which is at least one therapeutic agent selected from the group consisting of a therapeutic agent of arteriosclerosis, an anti-cancer drug, an anti-inflammatory agent, an immunosuppressant, a therapeutic agent of autoimmune disease, an anti-AIDS drug, a therapeutic agent of osteoporosis, a therapeutic agent of retinopathy, a brain function improving drug, a prophylactic agent of immature birth, a contraceptive and a prophylactic agent of digestive tract infection.

(9) A reagent having a Rho kinase inhibitory activity, which contains a compound of the formula (I), an isomer thereof and/or a pharmaceutically acceptable acid addition salt thereof.

(10) A diagnostic of a disease caused by Rho kinase, which contains a compound of the formula (I), an isomer thereof and/or a pharmaceutically acceptable acid addition salt thereof.

(11) A Rho kinase inhibitor containing a substituted isoquinolinesulfonamide derivative of the formula (II):

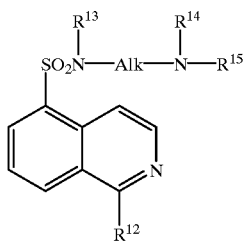

(II)

wherein $R^{12}$ is a hydrogen, a chlorine or a hydroxy, and when $R^{12}$ is a hydrogen, Alk is an alkylene having 2 to 6 carbon atoms, which optionally has alkyl having 1 to 10 carbon atoms, aryl or aralkyl as a substituent;

$R^{13}$ is a hydrogen;

$R^{14}$ is a hydrogen, or a linear or branched alkyl having 1 to 6 carbon atoms, an aryl or an aralkyl;

$R^{15}$ is a hydrogen, a linear or branched alkyl having 1 to 6 carbon atoms, an aryl or an aralkyl, or a benzoyl, a cinnamyl, a cinnamoyl, a furoyl or a group of the following formula:

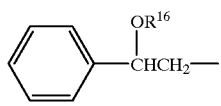

(j)

wherein $R^{16}$ is linear or branched alkyl having 1 to 6 carbon atoms or a group of the following formula:

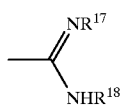

(k)

wherein $R^{17}$ and $R^{18}$ are hydrogen or directly bonded to form alkylene having 2 to 4 carbon atoms; or $R^{13}$ and $R^{14}$ are directly bonded to form alkylene having 4 or less carbon atoms, which is optionally substituted by alkyl having 1 to 10 carbon atoms, phenyl or benzyl, or $R^{14}$ and $R^{15}$ directly or in combination via oxygen atom form a heterocycle together with the adjacent nitrogen atom, and when $R^{12}$ is a chlorine or a hydroxy, Alk is an alkylene having 2 to 6 carbon atoms, which is optionally substituted at the hydrogen bonded to carbon by alkyl having 1 to 6 carbon atoms, $R^{13}$ and $R^{14}$ are each a hydrogen, a linear or branched alkyl having 1 to 6 carbon atoms or directly bonded to each other to form ethylene or trimethylene, wherein hydrogen bonded to carbon is optionally substituted by alkyl having 1 to 6 carbon atoms; or $R^{15}$ is a hydrogen, a linear or branched alkyl having 1 to 6 carbon atoms or an amidino, an isomer thereof and/or a pharmaceutically acceptable acid addition salt thereof.

(12) A pharmaceutical agent containing a compound of the formula (II), an isomer thereof and/or a pharmaceutically acceptable acid addition salt thereof, which is a therapeutic agent of at least one disease selected from the group consisting of hypertension, angina pectoris, cerebrovascular contraction, asthma, inflammation and, brain function disorder, which are caused by Rho kinase.

(13) A pharmaceutical agent containing a compound of the formula (II), an isomer thereof and/or a pharmaceutically acceptable acid addition salt thereof, which is at least one therapeutic agent selected from the group consisting of a therapeutic agent of peripheral circulation disorder, a therapeutic agent of arteriosclerosis, an anti-cancer drug, an immunosuppressant, a therapeutic agent of autoimmune disease, an anti-AIDS drug, a therapeutic agent of osteoporosis, a therapeutic agent of retinopathy, a prophylactic agent of immature birth, a contraceptive and a prophylactic agent of digestive tract infection.

(14) A reagent having a Rho kinase inhibitory activity, which contains a compound of the formula (II), an isomer thereof and/or a pharmaceutically acceptable acid addition salt thereof.

(15) A diagnostic for a disease caused by Rho kinase, which contains a compound of the formula (II), an isomer thereof and/or a pharmaceutically acceptable acid addition salt thereof.

(16) A compound of the formula (III):

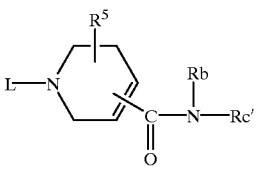

(III)

wherein Rc' is an optionally substituted heterocycle having nitrogen, which is other than pyridine of Rc, and other symbols are as defined above, an isomer thereof and/or a pharmaceutically acceptable acid addition salt thereof.

(17) The pharmaceutical agent of the above (1), containing a compound of the formula (III), an isomer thereof and/or a pharmaceutically acceptable acid addition salt thereof as a Rho kinase inhibitor.

(18) A pharmaceutical agent containing a compound of the formula (III), an isomer thereof and/or a pharmaceutically acceptable acid addition salt thereof, which is at least one therapeutic agent selected from the group consisting of a therapeutic agent of hypertension, a therapeutic agent of angina pectoris, a suppressive agent of cerebrovascular contraction, a therapeutic agent of asthma, a therapeutic agent of peripheral circulation disorder, a therapeutic agent of arteriosclerosis, an anti-cancer drug, an anti-inflammatory agent, an immunosuppressant, a therapeutic agent of autoimmune disease, an anti-AIDS drug, a therapeutic agent of osteoporosis, a therapeutic agent of retinopathy, a brain function improving drug, a prophylactic agent of immature birth, a contraceptive and a prophylactic agent of digestive tract infection.

(19) A pharmaceutical composition of the above (3), containing a compound of the formula (III), an isomer thereof and/or a pharmaceutically acceptable acid addition salt thereof as a Rho kinase inhibitor.

(20) A reagent having a Rho kinase inhibitory activity, which contains a compound of the formula (III), an isomer thereof and/or a pharmaceutically acceptable acid addition salt thereof as a Rho kinase inhibitor.

(21) A diagnostic for a disease caused by Rho kinase, which contains a compound of the formula (III), an isomer thereof and/or a pharmaceutically acceptable acid addition salt thereof.

(22) A method for treating a disease based on inhibition of Rho kinase, comprising administering a pharmaceutically effective amount of a Rho kinase inhibitor to a patient.

(23) The treating method of the above (22), wherein the disease treatable by the inhibition of the Rho kinase is at least one disease selected from the group consisting of hypertension, angina pectoris, cerebrovascular contraction, asthma, a peripheral circulation disorder, arteriosclerosis, cancer, an inflammation, an immune disease, an autoimmune disease, AIDS, osteoporosis, retinopathy, a brain function disorder, immature birth, fertilization and nidation of fertilized egg and infection of digestive tract.

(24) A method for treating at least one disease selected from the group consisting of hypertension, angina pectoris, cerebrovascular contraction, asthma and a peripheral circulation disorder, which are caused by Rho kinase, and arteriosclerosis, cancer, inflammation, immune disease, autoimmune disease, AIDS, osteoporosis, retinopathy, brain function disorder, immature birth, fertilization and nidation of fertilized egg and infection of digestive tract, which comprises administering a pharmaceutically effective amount of a compound of the formula (I), an isomer thereof and/or a pharmaceutically acceptable acid addition salt thereof.

(25) A method for treating at least one disease selected from the group consisting of hypertension, angina pectoris, cerebrovascular contraction, asthma, inflammation and brain function disorder, which are caused by Rho kinase, and a peripheral circulation disorder, arteriosclerosis, cancer, immune disease, autoimmune disease, AIDS, osteoporosis, retinopathy, immature birth, fertilization and nidation of fertilized egg and infection of digestive tract, which comprises administering a pharmaceutically effective amount of a compound of the formula (II), an isomer thereof and/or a pharmaceutically acceptable acid addition salt thereof.

(26) A method for treating at least one disease selected from the group consisting of hypertension, angina pectoris, cerebrovascular contraction, asthma, peripheral circulation disorder, arteriosclerosis, cancer, inflammation, immune disease, autoimmune disease, AIDS, osteoporosis, retinopathy, brain function disorder, immature birth, fertilization and nidation of fertilized egg and infection of digestive tract, which comprises administering a pharmaceutically effective amount of a compound of the formula (III), an isomer thereof and/or a pharmaceutically acceptable acid addition salt thereof.

(27) Use of a Rho kinase inhibitor for the production of a therapeutic agent of a disease treatable by inhibiting Rho kinase.

(28) The use of a Rho kinase inhibitor of the above (27), wherein the disease treatable by the inhibition of Rho kinase is at least one member selected from the group consisting of hypertension, angina pectoris, cerebrovascular contraction, asthma, peripheral circulation disorder, arteriosclerosis, cancer, inflammation, immune disease, autoimmune disease, AIDS, osteoporosis, retinopathy, brain function disorder, immature birth, fertilization and nidation of fertilized egg and infection of digestive tract.

(29) The use of a compound of the formula (I), an isomer thereof and/or a pharmaceutically acceptable acid addition salt thereof for the production of a therapeutic agent of at least one disease selected from the group consisting of hypertension, angina pectoris, cerebrovascular contraction, asthma and peripheral circulation disorder caused by Rho kinase, and arteriosclerosis, cancer, inflammation, immune disease, autoimmune disease, AIDS, osteoporosis, retinopathy, brain function disorder, immature birth, fertilization and nidation of fertilzed egg and infection of digestive tract.

(30) Use of a compound of the formula (II), an isomer thereof and/or a pharmaceutically acceptable acid addition salt thereof for the production of a therapeutic agent of at least one disease selected from the group consisting of hypertension, angina pectoris, cerebrovascular contraction, asthma, inflammation and brain function disorder caused by Rho kinase, and peripheral circulation disorder, arteriosclerosis, cancer, immune disease, autoimmune disease, AIDS, osteoporosis, retinopathy, immature birth, fertilization and nidation of fertilized egg and infection of digestive tract.

(31) Use of a compound of the formula (III), an isomer thereof and/or a pharmaceutically acceptable acid addition salt thereof for the production of a therapeutic agent of at least one disease selected from the group consisting of hypertension, angina pectoris, cerebrovascular contraction, asthma, peripheral circulation disorder, arteriosclerosis, cancer, inflammation, immune disease, autoimmune disease, AIDS, osteoporosis, retinopathy, brain function disorder, immature birth, fertilization and nidation of fertilized egg and infection of digestive tract.

(32) A commercial package comprising a Rho kinase inhibitor and a written matter associated therewith, the written matter stating that the Rho kinase inhibitor can or should be used for treating at least one disease selected from the group consisting of hypertension, angina pectoris, cerebrovascular contraction, asthma, peripheral circulation disorder, arteriosclerosis, cancer, inflammation, immune disease, autoimmune disease, AIDS, osteoporosis, retinopathy, brain function disorder, immature birth, fertilization and nidation of fertilized egg and infection of digestive tract.

(33) A commercial package comprising a compound of the formula (I), an isomer thereof and/or a pharmaceutically acceptable acid addition salt thereof and a written matter associated therewith, the written matter stating that the compound can or should be used for treating at least one disease selected from the group consisting of hypertension, angina pectoris, cerebrovascular contraction, asthma and peripheral circulation disorder, which are caused by Rho kinase, and arteriosclerosis, cancer, inflammation, immune disease, autoimmune disease, AIDS, osteoporosis, retinopathy, brain function disorder, immature birth, fertilization and nidation of fertilized egg and infection of digestive tract.

(34) A commercial package comprising a compound of the formula (II), an isomer thereof and/or a pharmaceutically acceptable acid addition salt thereof and a written matter associated therewith, the written matter stating that the compound can or should be used for treating at least one disease selected from the group consisting of hypertension, angina pectoris, cerebrovascular contraction, asthma, inflammation and brain function disorder, which are caused by Rho kinase, and peripheral circulation disorder, arteriosclerosis, cancer, immune disease, autoimmune disease, AIDS, osteoporosis, retinopathy, immature birth, fertilization and nidation of fertilized egg and infection of digestive tract.

(35) A commercial package comprising a compound of the formula (III), an isomer thereof and/or a pharmaceutically acceptable acid addition salt thereof and a written matter associated therewith, the written matter stating that the compound can or should be used for treating at least one disease selected from the group consisting of hypertension, angina pectoris, cerebrovascular contraction, asthma, peripheral circulation disorder, arteriosclerosis, cancer, inflammation, immune disease, autoimmune disease, AIDS, osteoporosis, retinopathy, brain function disorder, immature birth, fertilization and nidation of fertilized egg and infection of digestive tract.

DETAILED DESCRIPTION OF THE INVENTION

The Rho kinase inhibitory action, antihypertensive action, anti-angina pectoris action, cerebrovascular contraction suppressive action, anti-asthma action, peripheral circulation improving action, immature birth preventive action, anti-arteriosclerosis action, anti-cancer action, antiinflammatory action, immunosuppressive action, autoimmune disease improving action, anti-AIDS action, preventive action of fertilization and nidation of fertilized egg, preventive action on bacterial infection of digestive tract, osteoporosis treating action, retinopathy treating action and brain function improving action of the present invention can be confirmed by Rho kinase inhibitory activity, vasohypotonic action, trachea relaxing action, peripheral blood flow increasing action, cell adhesion induction inhibitory action, malignant tumor metastasis inhibitory action, bone resorption inhibitory action, mouse allogenic MLR inhibitory activity, tumor cell proliferation inhibitory action, angiogenesis inhibitory action, vascular smooth muscle cell proliferation inhibitory action and the like.

The disease relating to Rho, on which the inventive Rho kinase inhibitor is effective include, for example, disease symptoms of hypertension, angina pectoris, cerebrovascular contraction, asthma, peripheral circulation disorder, immature birth, arteriosclerosis, cancer, inflammation, immune disease, autoimmune disease, AIDS, bacterial infection of digestive tract, osteoporosis, retinopathy, brain function disorder and the like, as well as biological phenomena such as fertilization and nidation of fertilized egg.

As used herein, by the Rho kinase of the present invention is meant serine/threonine kinase activated along with the activation of Rho, which is exemplified by the aforementioned ROCα(ROCKII), p160ROCK(ROCβ, ROCK-I) and other proteins having serine/threonine kinase activity.

Cancer includes bone marrow leukemia, lymphocytic leukemia, gastric cancer, colon cancer, lung cancer, pancreatic cancer, liver cancer, cancer of esophangus, ovarian cancer, breast cancer, skin cancer, cervical cancer, orchioncus, neuroblastoma, urinary epithelial cancer, multiple myeloma, uterine cancer, melanoma, cerebral tumor and the like, and anti-cancer means inhibition of formation, infiltration, metastasis, growth and the like of these tumors.

The immune disease includes allergic diseases, rejection in organ transplantation and the like.

The autoimmune disease includes articular rheumatism, systemic lupus erythematodes, Sjögren's disease, multiple sclerosis, myasthenia gravis, type I diabetes, endocrine ophthalmopathy, primary biliary cirrhosis, Crohn's disease, glomerulonephritis, sarcoidosis, psoriasis, pemphigus, hyoplastic anemia, essential thrombocytopenic purpura and the like.

Bacterial infection of digestive tract means various diseases caused by the invasion of Salmonella, dysentery bacillus, intestinal pathogenic *Escherichia coli* and the like into intestinal mucosa epithelial cells.

Retinopathy means angiopathic retinopathy, arteriosclerosis retinopathy, central angiospastic retinopathy, central serous retinopathy, circinate retinopathy, diabetic retinopathy, dysproteinemic retinopathy, hypertensive retinopathy, leukemic retinopathy, lipemic retinopathy, proliferative retinopathy, renal retinopathy, sickde retinopathy, toxemic retinopathy of pregnancy and the like.

Brain function disorder includes psychotic condition due to cerebral hemorrhage, cerebral thrombus, cerebral embolus, subarachnoid hemorrhage, transient cerebral ischemic stroke, hypertensive encephalopathy, cerebral arteriosclerosis, subdural hematoma, extradural hematoma, cerebral hypoxia, cerebral edema, cerebritis, cerebral tumor, external injuiy in head, mental disease, metabolite poisoning, drug poisoning, temporal respiratory arrest, deep anesthesia during operation, physical disorder and the like, and sequelae, decreased attention, hyperactivity, logopathy, delayed mental development, lethe, dementia (inclusive of wandering, nocturnal delirium, aggressive behavior and the like associated with dementia) caused by the above-mentioned diseases.

Therefore, the Rho kinase inhibitor of the present invention is effective as a pharmaceutical agent, particularly as an agent for the prophylaxis and treatment of these diseases caused by Rho, such as a therapeutic agent of hypertension, a therapeutic agent of angina pectoris, a suppressive agent of cerebrovascular contraction, a therapeutic agent of asthma, a therapeutic agent of peripheral circulation disorder, a prophylactic agent of immature birth, a therapeutic agent of arteriosclerosis, an anti-cancer drug, an anti-inflammatory agent, an immunosuppressant, a therapeutic agent of autoimmune disease, an anti-AIDS drug, a contraceptive, a prophylactic agent of digestive tract infection, a therapeutic agent of osteoporosis, a therapeutic agent of retinopathy and a brain function improving drug.

The compounds of the formula (I) and the formula (II) have high affinity for Rho kinase. Thus, the radioactive substance (radio ligand) thereof are industrially useful as a selective radio ligand of Rho kinase. The compounds of the formula (I) and the formula (II) and modified compounds thereof (e.g., radio ligand of these compounds and the like), which are Rho kinase inhibitors, are useful as reagents for the study of Rho and Rho kinase and as diagnostics of the diseases relating to them.

The compound to be used as the Rho kinase inhibitor of the present invention may be any as long as it has a Rho linase inhibitory action. For example, the compounds of the formula (I) and the formula (II) are used.

In the present specification, each symbol of the formula (I is defined as follows.

Alkyl at R and $R^1$ is linear or branched alkyl having 1 to 10 carbon atoms, which is exemplified by methyl, ethyl, propyl, isopropyl, butyl, isobutyl, sec-butyl, tert-butyl, pentyl, hexyl, heptyl, octyl, nonyl, decyl and the like, with preference given to alkyl having 1 to 4 carbon atoms.

Cycloalkyl at R and $R^1$ has 3 to 7 carbon atoms and is exemplified by cyclopropyl, cyclobutyl, cyclopentyl, cyclohexyl, cycloheptyl and the like.

Cycloalkylalkyl at R and $R^1$ is that wherein the cycloalkayl moiety is the above-mentioned cycloalkyl having 3 to 7 carbon atoms and the alkyl moiety is linear or branched alkyl having 1 to 6 carbon atoms (e.g., methyl, ethyl, propyl, isopropyl, butyl, pentyl, hexyl and the like), which is exemplified by cyclopropylmethyl, cyclobutylmethyl, cyclopentylmethyl, cyclohexylmethyl, cycloheptylmethyl, cyclopropylethyl, cyclopentylethyl, cyclohexylethyl, cycloheptylethyl, cyclopropylpropyl, cyclopentylpropyl, cyclohexylpropyl, cycloheptylpropyl, cyclopropylbutyl, cyclopentylbutyl, cyclohexylbutyl, cycloheptylbutyl, cyclopropylhexyl, cydopentylhexyl, cyclohexylhexyl, cycloheptylhexyl and the like.

Aralkyl at R and $R^1$ is that wherein alkyl moiety is alkyl having 1 to 4 carbon atoms and is exemplified by phenylalkyl such as benzyl, 1-phenylethyl, 2 -phenylethyl, 3-phenylpropyl, 4-phenylbutyl and the like.

The substituent of optionally substituted cycloalkyl, cycloalkylalkyl, phenyl and aralkyl on the ring at R and $R^1$ is halogen (e.g., chlorine, bromine, fluorine and iodine), alkyl (same as alkyl at R and $R^1$), alkoxy (linear or branched alkoxy having 1 to 6 carbon atoms, such as methoxy, ethoxy, propoxy, isopropoxy, butoxy, isobutoxy, sec-butoxy, tert-butoxy, pentyloxy, hexyloxy and the like), aralkyl (same as aralkyl at R and $R^1$) or haloalkyl (alkyl at R and $R^1$ which is substituted by 1–5 halogen, and exemplified by fluoromethyl, difluoromethyl, trifluoromethyl, 2,2,2-trifluoroethyl, 2,2,3,3,3-pentafluoropropyl and the like), nitro, amino, cyano, azide and the like.

The group formed by R and $R^1$ in combination together with the adjacent nitrogen atom, which forms a heterocycle optionally having, in the ring, oxygen atom, sulfur atom or optionally substituted nitrogen atom is preferably a 5 or 6-membered ring and bonded ring thereof. Examples thereof include 1-pyrrolidinyl, piperidino, 1-piperazinyl, morpholino, thiomorpholino, 1-imidazolyl, 2,3-dihydrothiazol-3-yl and the like. The substituent of the optionally substituted nitrogen atom is exemplified by alkyl, aralkyl, haloalkyl and the like. As used herein, alkyl, aralkyl and haloalkyl are as defined for R and $R^1$.

Alkyl at $R^2$ is as defined for R and $R^1$.

Halogen, alkyl, alkoxy and aralkyl at $R^3$ and $R^4$ are as defined for R and $R^1$.

Acyl at $R^3$ and $R^4$ is alkanoyl having 2 to 6 carbon atoms (e.g., acetyl, propionyl, butyryl, valeryl, pivaloyl and the like), benzoyl or phenylalkanoyl wherein the alkanoyl moiety has 2 to 4 carbon atoms (e.g., phenylacetyl, phenylpropionyl, phenylbutyryl and the like).

Alkylamino at $R^3$ and $R^4$ is that wherein the alkyl moiety is alkylamino having linear or branched alkyl having 1 to 6 carbon atoms. Examples thereof include methylamino, ethylamino, propylanino, isopropylamino, butylamino, isobutylamino, sec-butylamino, tert-butylamino, pentylamino, hexylamino and the like.

Acylamino at $R^3$ and $R^4$ is that wherein acyl moiety is alkanoyl having 2 to 6 carbon atoms, benzyl or the alkanoyl moiety is phenylalkanoyl having 2 to 4 carbon atoms and the like, which is exemplified by acetylamino, propionylamino, butyrylamino, valerylamino, pivaloylamino, benzoylamino, phenylacetylamino, phenylpropionylamino, phenylbutyrylamino and the like.

Alkylthio at $R^3$ and $R^4$ is that wherein the alkyl moiety is linear or branched alkyl having 1 to 6 carbon atoms, which is exemplified by methylthio, ethylthio, propylthio, isopropylthio, butylthio, isobutylthio, sec-butylthio, tert-butylthio, pentylthio, hexylthio and the like.

Aralkyloxy at $R^3$ and $R^4$ is that wherein the alkyl moiety is alkyl having 1 to 4 carbon atoms, which is exemplified by benzyloxy, 1-phenylethyloxy, 2-phenylethyloxy, 3-phenylpropyloxy, 4-phenylbutyloxy and the like.

Aralkythio at $R^3$ and $R^4$ is that wherein the alkyl moiety is alkyl having 1 to 4 carbon atoms, which is exemplified by benzylthio, 1-phenylethylthio,2-phenylethylthio,3-phenylpropylthio,4-phenylbutylthio and the like.

Alkoxycarbonyl at $R^3$ and $R^4$ is that wherein the alkoxy moiety is linear or branched alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Alkylcarbamoyl at $R^3$ and $R^4$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

Alkoxy at $R^5$ is as defined for R and $R^1$.

Alkoxycarbonyloxy at $R^5$ is that wherein the alkoxy moiety is linear or branched alkoxy having 1 to 6 carbon atoms, which is exemplified by methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tertbutoxycarbonyloxy, pentyloxycarbonyloxy, hexyloxycarbonyloxy and the like.

Alkanoyloxy at $R^5$ is that wherein the alkanoyl moiety is alkanoyl having 2 to 6 carbon atoms, which is exemplified by acetyloxy, propionyloxy, butyryloxy, valeryloxy, pivaloyloxy and the like.

Aralkyloxycarbonyloxy at $R^5$ is that wherein the aralkyl moiety is aralkyl having $C_1-C_4$ alkyl, which is exemplified by benzyloxycarbonyloxy, 1-phenylethyloxycarbonyloxy, 2-phenylethyloxycarbonyloxy, 3-phenylpropyloxycarbonyloxy, 4-phenylbutyloxycarbonyloxy and the like.

Alkyl at $R^6$ is as defined for R and $R^1$; alkyl at $R^8$ and $R^9$ is as defined for R and $R^1$; and aralkyl at $R^8$ and $R^9$ is as defined for R and $R^1$.

Alkyl at $R^7$ is as defined for R and $R^1$ and aralkyl at $R^7$ is as defined for R and $R^1$.

The group formed by $R^6$ and $R^7$ in combination, which forms a heterocycle optionally having, in the ring, oxygen atom, sulfur atom or optionally substituted nitrogen atom, is imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl or optionally substituted benzoimidazol-2-yl, benzothiazol-2-yl, benzoxazol-2-yl and the like having a substituent such as halogen, alkyl, alkoxy, haloalkyl, nitro, amino, phenyl, aralkyl and the like. As used herein, halogen, alkyl, alkoxy, haloalkyl and aralkyl are as defined for R and $R^1$.

The substituent of the above-mentioned optionally substituted nitrogen atom is exemplified by alkyl, aralkyl, haloalkyl and the like. As used herein, alkyl, aralkyl and haloalkyl are as defined for R and $R^1$.

Hydroxyalkyl at $R^{10}$ and $R^{11}$ is linear or branched alkyl having 1 to 6 carbon atoms which is substituted by 1 to 3 hydroxy, which is exemplified by hydroxymethyl, 2-hydroxyethyl, 1-hydroxyethyl, 3-hydroxypropyl, 4-hydroxybutyl and the like. Alkyl at $R^{10}$ and $R^{11}$ is as defined for R and $R^1$; haloalkyl and alkoxycarbonyl at $R^{10}$ and $R^{11}$ are as defined for R and $R^1$; aralkyl at $R^{10}$ and $R^{11}$ is as defined for R and $R^1$; and cycloalkyl formed by $R^{10}$ and $R^{11}$ in combination is the same as cycloalkyl at R and $R^1$.

Alkyl at L is as defined for R and $R^1$.

Aminoalky at L is a linear or branched alkyl having 1 to 6 carbon atoms, which is substituted by amino, which is exemplified by aminomethyl, 2-aminoethyl, 1-aminoethyl, 3-aminopropyl, 4-aminobutyl, 5-aminopentyl, 6-aminohexyl and the like.

Mono- or dialkylaminoalkyl at L is mono- or di-substituted aminoalkyl with alkyl having 1 to 4 carbon atoms, which is exemplified by methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylainioethyl and the like.

Carbamoylalkyl at L is linear or branched alkyl having 1 to 6 carbon atoms substituted by carbamoyl, which is exemplified by carbamoylmethyl, 2-carbamoylethyl, 1-carbamoylethyl, 3-carbamoylpropyl, 4-carbamoylbutyl, 5-carbamoylpentyl, 6-carbamoylhexyl and the like.

Phthalimidoalkyl at L is linear or branched alkyl having 1 to 6 carbon atoms, which is substituted by phthalmide. Examples thereof include phthalimidomethyl, 2-phthalimidoethyl, 1-phthalimidoethyl, 3-phthalimidopropyl, 4-phthalimidobutyl, 5-phthalimidopentyl, 6-phthaimidohexyl and the like.

Alkyl at B is as defined for R and $R^1$.

Alkoxy at B is as defined for R and $R^1$.

Aralkyl at B is as defined for R and $R^1$.

Aralkyloxy at B is as defined for $R^3$ and $R^4$.

Aminoalkyl at B is as defined for L.

Hydroxyalkyl at B is as defined for $R^{10}$ and $R^{11}$.

Alkanoyloxyakyl at B is that wherein linear or branched alkyl having 1 to 6 carbon atoms is substituted by alkanoyloxy having alkanoyl moiety having 2 to 6 carbon atoms, which is exemplified by acetyloxymethyl, propionyloxymethyl, butyryloxymethyl, valeryloxymethyl, pivaloyloxymethyl, acetyloxyethyl, propionyloxyethyl, butyryloxyethyl, valeryloxyethyl, pivaloyloxyethyl and the like.

Alkoxycarbonylalkyl at B is that wherein linear or branched alkyl having 1 to 6 carbon atoms is substituted by alkoxycarbonyl having alkoxy moiety having 1 to 6 carbon atoms, which is exemplified by methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, pentyloxycarbonylmethyl, hexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, sec-butoxycarbonylethyl, tert-butoxycarbonylethyl, pentyloxycarbonylethyl, hexyloxycarbonylethyl and the like.

Halogen at $Q^1$, $Q^2$ and $Q^3$ is as defined for R and $R^1$.

Aralkyloxy at $Q^1$ and $Q^2$ is as defined for $R^3$ and $R^4$.

Alkoxy at $Q^3$ is as defined for R and $R^1$.

Alkylene at W, X and Y is linear or branched alkylene having 1 to 6 carbon atoms, which is exemplified by methylene, ethylene, timethylene, propylene, tetramethylene, pentamethylene, hexamethylene and the like.

Alkenylene at Y is linear or branched alkenylene having 2 to 6 carbon atoms, which is exemplified by vinylene, propenylene, butenylene, pentenylene and the like.

Alkyl at Rb is as defined for R and $R^1$.

Aralkyl at Rb is as defined for R and $R^1$.

Aminoalkyl at Rb is as defined for L.

Mono- or dialkylaminoakl at Rb is as defined for L.

The heterocycle when single ring containing nitrogen at Rc is pyridine, pyrimidine, pyridazine, triazine, pyrazole, triazole and the like, and when it is a condensed ring, it is exemplified by pyrrolopyridine (e.g., 1H-pyrrolo[2,3-b]pyridine, 1H-pyrrolo[3,2-b]pyridine, 1H-pyrrolo[3,4-b]pyridine and the like), pyrazolopyridine (e.g., 1H-pyrazolo[3,4-b]pyridine, 1H-pyrazolo[4,3-b]pyridine and the like), imidazopyridine (e.g., 1H-imidazo[4,5-b]pyridine and the like), pyrrolopyrimidine (e.g., 1H-pyrrolo[2,3-d]pyrimidine, 1H-pyrnolo[3,2-d]pyrimidine, 1H-pyrrolo[3,4-d]pyrimidine and the like), pyrazolopyrimidine (e.g., 1H-pyrazolo[3,4-d]pyrimidine, pyrazolo[1,5-a[pyrimidine, 1H-pyrazolo]4,3-d]pyrimidine and the like), imidazopyrimidine (e.g., imidazol[1,2-a]pyrimidine, 1H-imidazo[4,5-d]pyrmidine and the like), pyrrolotriazine (e.g., pyrrolo[1,2-a]-1,3,5-triazine, pyrrolo[2,1-f]-1,2,4-triazine), pyrazolotriazine (e.g., pyrazolo[1,5-a]-1,3,5-triazine and the like), triazolopyridine (e.g., 1H-1,2,3-triazolo[4,5-b]pyridine and the like), triazolopyrimidine (e.g., 1,2,4-triazolo[1,5-a]pyrimidine, 1,2,4-triazolo[4,3-a]pyrimidine, 1H-1,2,3-triazolo[4,5-d]pyrimidine and the like), cinnoline, quinazoline, quinoline, pyridopyridazine (e.g., pyrido[2,3-c]pyridazine and the like), pyridopyrazine (e.g., pyrido[2,3-b]pyrazine and the like), pyridopyrimidine (e.g., pyrido[2,3-d]pyrimidine, pyrido[3,2-d]pyrimidine and the like), pyrimidopyrimidine (e.g., pyrimido[4,5-d]pyrimidine, pyrimiido[5,4-d]pyrimidine and the like), pyrazinopyrimidine (e.g., pyrazino[2,3-d]pyrimidine and the like), naphthyridine (e.g., 1,8-naphthyridine and the like), tetrazolopyrimidine (e.g., tetrazolo[1,5-a]pyrimidine and the like), thienopyridine (e.g., thieno[2,3-b]pyridine and the like), thienopyrimidine (e.g., thieno[2,3-d]pyrimidine and the like), thiazolopyridine (e.g., thiazolo[4,5-b]pyridine, thiazolo[5,4-b]pyridine and the like), thiazolopyrimidine (e.g., thiazolo[4,5-d]pyrimidine, thiazolo[5,4-d]pyrimidine and the like), oxazolopyridine (e.g., oxazolo[4,5-b]pyridine, oxazolo[5,4-b]pyridine and the like), oxazolopyrimidine (e.g., oxazolo[4,5-d]pyrimidine, oxazolo[5,4-d]pyrimidine and the like), furopyridine (e.g., furo[2,3-b]pyridine, furo[3,2-b]pyridine and the like), furopyrimidine (e.g., furo[2,3-d]pyrinidine, furo[3,2-d]pyrimidine and the like), 2,3-dihydropyrrolopyridine (e.g., 2,3-dihydro-1H-pyrrolo[2,3-b]pyridine, 2,3-dihydro-1H-pyrrolo[3,2-b]pyridine and the like), 2,3-dihydropyrrolopyrimidine (e.g., 2,3-dihydro-1H-pyrrolo[2,3-d]pyrimidine, 2,3-dihydro-1H-pyrrolo[3,2-d]

pyrimidine and the like), 5,6,7,8-tetrahydropyiido[2,3-d] pyrimidine, 5,6,7,8-tetrahydro-1,8-naphthyridine, 5,6,7,8-tetrahydroquinoline and the like. When these rings form a hydrogenated aromatic ring, the carbon atom in the ring may be carbonyl and includes, for example, 2,3-dihydro-2-oxopyrrolopyridine, 2,3-dihydro-2,3-dioxopyrrolopyridine, 7,8-dihydro-7-oxo-1,8-naphthyridine, 5,6,7,8-tetrahydro-7-oxo-1,8-naphthyridine and the like.

These rings may be substituted by a substituent such as halogen, alkyl, alkoxy, aralkyl, haloalkyl, nitro, amino, alkylamino, cyano, formyl, acyl, aminoalkyl, mono- or dialkylaminoalkyl, azide, carboxy, alkoxycarbonyl, carbamoyl, alkylcarbamoyl, alkoxyalkyl (e.g., methoxymethyl, methoxyethyl, methoxypropyl, ethoxymethyl, ethoxyethyl, ethoxypropyl and the like), optionally substituted hydrazino and the like.

As used herein, the substituent of the optionally substituted hydrazino includes alkyl, aralkyl, nitro, cyano and the like, wherein alkyl and aralkyl are as defined for R and $R^1$ and exemplified by methyl hydrazino, ethyl hydrao, benzyl hydrazino and the like.

In the present specification, each symbol of the formula (II) is defined as follows.

The linear or branched alkyl having 1 to 6 carbon atoms at $R^{13}$, $R^{14}$, $R^{15}$ and $R^{16}$ is methyl, ethyl, propyl, isopropyl, butyl, isobutyl, sec-butyl, tert-butyl, pentyl, hexyl and the like.

Aryl at $R^{14}$ and $R^{15}$ is phenyl, naphthyl and the like.

Aralkyl at $R^{14}$ and $R^{15}$ is as defined for R and $R^1$.

Alkylene having 4 or less carbon atoms, which is formed by $R^{13}$ and $R^{14}$ directly bonded to each other, is methylene, ethylene, trimethylene, propylene, tetramethylene and the like.

Alkyl having 1 to 10 carbon atoms, which substitutes alkylene having 4 or less carbon atoms formed by $R^{13}$ and $R^{14}$ directly bonded to each other, is linear or branched alkyl having 1 to 10 carbon atoms. Examples thereof include methyl, ethyl, propyl, isopropyl, butyl, isobutyl, sec-butyl, tert-butyl, pentyl, hexyl, heptyl, octyl, nonyl, decyl and the like.

Alkyl having 1 to 6 carbon atoms which substitutes ethylene and trimethylene formed by $R^{13}$ and $R^{14}$ directly bonded to each other is linear or branched alkyl having 1 to 6 carbon atoms, which is the same as those for $R^{13}$.

The heterocycle formed by $R^{14}$ and $R^{15}$ directly or via oxygen atom bonded together with the adjacent nitrogen atom is pyrrolidino, piperidino, morpholino, homopiperidino, homomorpholino and the like.

Alkylene having 2 to 4 carbon atoms formed by $R^{17}$ and $R^{18}$ directly bonded to each other is ethylene, trimethylene, propylene, tetramethylene and the like.

Alkylene having 2 to 6 carbon atoms at Alk is ethylene, trimethylene, propylene, tetramethylene, pentamethylene, hexamethylene and the like.

Alkyl having 1 to 6 carbon atoms and alkyl having 1 to 10 carbon atoms, which are the substituents of alkylene having 2 to 6 carbon atoms atalkyl, are as defined for $R^{13}$.

Aryl and aralkyl, which are the substituents of alkylene having 2 to 6 carbon atoms at alkyl are as defined for $R^{14}$.

The compound to be used as the Rho kinase inhibitor of the present invention is, for example, a compound of the formula (I), which is exemplified by the following compounds.

(1) 4-(2-pyridylcarbamoyl)piperidine
(2) 1-benzyloxycarbonyl-4-(4-pyridylcarbamoyl)piperidine
(3) 1-benzoyl-4-(4-pyridylcarbamoyl)piperidine
(4) 1-propyl-4-(4-pyridylcarbamoyl)piperidine
(5) [3-(2-(2-thienylmethyl)phenoxy)-2-hydroxypropyl]-4-(4-pyridylcarbamoyl)piperidine
(6) 4-(4-pyridylcarbamoyl)piperidine
(7) 1-benzyl-4-(4-pyridylcarbamoyl)-1,2,5,6-tetrahydropyridine
(8) 3-(4-pyridylcarbamoyl)piperidine
(9) 1-benzyl-3-(4-pyridylcarbamoyl)piperidine
(10) 1-(2-(4-benzyloxyphenoxy)ethyl)-4-(N-(2-pyridyl)-N-benzylcarbamoyl)pyridine
(11) 1-formyl-4-(4-pyridylcarbamoyl)piperidine
(12) 4-(3-pyridylcarbamoyl)piperidine
(13) 1-isopropyl-4-(4-pyridylcarbamoyl)piperidine
(14) 1-methyl-4-(4-pyridylcarbamoyl)piperidine
(15) 1-hexyl-4-(4-pyridylcarbamoyl)piperidine
(16) 1-benzyl-4-(4-pyridylcarbamoyl)piperidine
(17) 1-(2-phenylethyl)-4-(4-pyiidylcarbamoyl)piperidine
(18) 1-(2-(4-methoxyphenyl)ethyl)-4-(4-pyridylcarbamoyl)piperidine
(19) 1-(2-(4-methoxyphenyl)ethyl)-4-(2-pyridylcarbamoyl)pipelidine
(20) 1-(2-(4-chlorophenyl)ethyl)-4-(4-pyridylcarbamoyl)piperidine
(21) 1-diphenylmethyl-4-(2-pyridylcarbamoyl)piperidine
(22) 1-[2-(4-(5-methyl-3-oxo-2,3,4,5-tetruhydropyridazin-6-yl)phenyl)ethyl]-4-(2-pyridylcarbamoyl)piperidine
(23) 1-(4-(4,5-dihydro-2-furyl)phenyl)-4-(4-pyridylcarbamoyl)piperidine
(24) 1-(2-nitrophenyl)-4-(4-pyridylcarbamoyl)pipexidine
(25) 1-(2-aminophenyl)-4-(4-pyridylcarbamoyl)piperidine
(26) 1-nicotinoyl-4-(4-pyridylcarbamoyl)piperidine
(27) 1-isonicotinoyl-4-(4-pyridylcarbamoyl)piperidine
(28) 1-(3,4,5-trihethoxybenzoyl)-4-(4-pyridylcarbamoyl)piperidine
(29) 1-acetyl-4-(4-pyridylcarbamoyl)piperidine
(30) 1-(3-(4-fluorobenzoyl)propy)-4-(4-pyridylcarbamoyl)piperldine
(31) 1-(3-(4-fluorobenzoyl)propyl)-4-(2-pytidylcarbamoyl)piperidine
(32) 1-(1-(4-hydroybenzoyl)ethyl)-4-(2-pyridylcarbamoyl)piperidine
(33) 1-(1-(4-benzyloxybenzoyl)ethyl)-4-(2-pyridylcarbamoyl)pipexidine
(34) 1-(2-(4-hydroxyphenoxy)ethyl)-4-(2-pyridylcarbamoyl)pipendine
(35) 1-(4-(4-fluorophenyl)-4-hydroxybutyl)-4-(4-pyridylcarbamoyl)piperidine
(36) 1-(1-methyl-2-(4-hydroxyphenyl)-2-hydroxyethyl)-4-(2-pyridylcarbamoyl)piperidine
(37) 1-cinnamyl-4-(2-pyridylcarbamoyl)piperidine
(38) 1-(2-hydroxy-3-phenoxypropyl)-4-(4-pyridylcarbamoyl)piperidine
(39) 1-(2-hydroxy-3-phenoxypropyl)-4-(3-pyridylcarbamoyl)piperidine
(40) 1-(2-hydroxy-3-phenoxypropyl)-4-(2-pyridylcarbamoyl)piperidine
(41) 1-(2-phenylethyl)-4-[N-(2-pyridyl)-N-(2-(N,N-dimethylamino)ethyl)-carbamoyl]piperidine
(42) 1-benzyloxycarbonyl-4-(2-pyridylcarbamoyl)piperidine
(43) 1-(3-chlorophenyl)carbamoyl-4-(4-pyridylcarbamoyl)piperidine
(44) 1-[N-(2-pyridyl)-N-(2-(N,N-dimethy amino)ethyl)carbamoyl]piperidine

(45) 1-methyl-4-(4-pyridylcarbamoyl)-1,2,5,6-tetrahydropyridine
(46) 1-nicotinoyl-3-(4-pyridylcarbamoyl)piperidine
(47) 1-[2-(4-fluorobenzoyl)ethyl]-4-(4-pyridylcarbamoyl)piperidine
(48) 1-(6-chloro-2-methylimidazo[1,2-a]pyridine-3-carbonyl)-4-(4-pyridylcarbamoyl)piperidine
(49) 1-(4-nitrobenzyl)-4-(4-pyridylcarbamoyl)pipenidine
(50) 1-hexyl-4-(4-pyridylcarbamoyl)piperidine
(51) 1-benzyloxycarbonyl-4-(2-chloro-4-pyridylcarbamoyl)piperidine
(52) 4-(2-chloro-4-pyridylcarbamoyl)piperidine
(53) 1-(2-chloronicotinoyl)-4-(4-pyridylcarbamoyl)piperidine
(54) 3-(2-chloro-4-pyridylcarbamoyl)piperidine
(55) 1-(4-phthalimidobutyl)-4-(4-pyridylcarbamoyl)piperidine
(56) 1-(3,5-di-tert-butyl-4-hydroxycinnamoyl)-4-(4-pyridylcarbamoyl)piperidine
(57) 1-carbamoylmethyl-4-(4-pyridylcarbamoyl)piperidine
(58) 1-benzyloxycarbonyl-4-(5-nitro-2-pyridylcarbamoyl)piperidine
(59) 4-(5-nitro-2-pyridylcarbamoyl)piperidine
(60) trans-4-benzyloxycarboxamidomethyl-1-(4-pyridylcarbamoyl)cyclohexane
(61) trans-4-aminomethyl-1-(4-pyridylcarbamoyl)cydohexane
(62) trans-4-formamidomethyl-1-(4-pyridylcarbamoyl)cyclohexane
(63) trans-4-dimethyaminomethyl-1-(4-pyridylcarbamoyl)cyclohexane
(64) N-benzylidene-trans-(4-pyridylcarbamoyl)cyclohexylmethy amie
(65) trans-4-benzylaminomethyl-1-(4-pyridylcarbamoyl)cyclohexane
(66) trans-4-isopropylaminomethyl-1-(4-pyridylcarbamoyl)cyclohexane
(67) trans-4-nicotinoylaminomethyl-1-(4-pyridylcarbamoyl)cyclohexane
(68) trans-4-cylohexylaminomethyl-1-(4-pyridylcarbamoyl)cyclohexane
(69) trans-4-benzyloxycarboxamide-1-(4-pyridylcarbamoyl)cyclohexane
(70) trans-4-amino-1-(4-pyridylcarbamoyl)cyclohexane
(71) trans-4-(1-aminoethyl)-1-(4-pyridylcarbamoyl)cyclohexane
(72) trans-4-aminomethyl-cis-2-methyl-1-(4-pyridylcarbamoyl)cyclohexane
(73) (+)-trans-4-(1-benzyloxycarboxamidopropyl)-1-cyclohexanecarboxylic acid
(74) (+)-trans-4-(1-benzyloxycarboxamidopopyl)-1-(4-pyridylcarbamoyl)cyclohexane
(75) (−)-trans-4-(1-benzyloxycarboxamidpropyl)-1-(4-pyridylcarbamoyl)cyclohexane
(76) (+)-trans-4-(1-aminopropyl)-1-(4-pyridylcarbamoyl)cyclohexane
(77) (−)-trans-4-(1-aminopropyl)-1-(4-pyridylcarbamoyl)cyclohexane
(78) (−)-trans-4-(1-benzyloxycarboxamidoethyl)-1-(4-pyridylcarbamoyl)cyclohexane
(79) (+)-trans-4-(1-benzyloxycarboxamidoethyl)-1-(4-pyridylcarbamoyl)cyclohexane
(80) (+)-trans-4-(1-aminoethyl)-1-(4-pyridylcarbamoyl)cyclohexane
(81) (+)-trans-4-(1-aminoethyl)-1-(4-pyridylcarbamoyl)cyclohexane
(82) trans-4-(4-chlorobenzoyl)aminomethyl-1-(4-pyridylcarbarnoyl)cyclohexne
(83) trans-4-aminomethyl-1-(2-pyridylcarbamoyl)cyclohexane
(84) trans-4-benzryoxycarboxamidomethyl-1-(2-pyridylcarbamoyl)cyclohexane
(85) trans-4-methylaminomethyl-1-(4-pyridylcarbaroyl)cyclohexane
(86) trans-4(N-benzyl-N-methylamino)methyl-1-(4-pyridylcarbamoyl)cylohexane
(87) trans-4-aminomethyl-1-(3-pyridylcarbamoyl)cyclohexane
(88) trans-4-aminomethyl-1-[(3-hydroxy-2-pyridyl)carbamoyl]cyclohexane
(89) trans-4-benzyloxycarboxamidomethyl-1-(3-pyridylcarbamoyl)cyclohexane
(90) trans-4-benzyloxycarboxamidomethyl-1-[(3-benzyloxy-2-pyridyl)carbamoyl]cyclohexane
(91) trans-4-phthalimidomethyl-1-(4-pyridylcarbamoyl)cyclohexane
(92) trans-4-benzyloxycarboxamidomethyl-1-(3-methyl-4-pyridylcarbamoyl)cyclohexane
(93) trans-4-aminomethyl-1-(3-methyl-4-pyridylcarbamoyl)cyclohexane
(94) 4-(trans-4-benzyloxycarboxamidomethylcyclohexylcarbonyl)amino-2,6-dimethylpyridine-N-oxide
(95) 4-(trans-4-aminomethylcyclohexylcarbonyl)amino-2,6-dimethylpyridine-N-oxide
(96) trans-4-aminomethyl-1-(2-methyl-4-pyridylcarbamoyl)cyclohexane
(97) trans-4-(1-benzyloxycarboxamidomethyl)-1-(4-pyridylcarbamoyl)cyclohexane
(98) trans-4-(1-amino-1-methylethyl)-1-(4-pyridylcarbamoyl)cyclohexane
(99) trans-4-(2-aminoethyl)-1-(4-pyridylcarbamoyl)cyclohexane
(100) trans-4-(2-amino-1-methylethyl)-1-(4-pyridylcarbamoyl)cyclohexane
(101) trans-4-(1-aminopropyl)-1-(4-pyridylcarbamoyl)cyclohexane
(102) trans-4-aminomethyl-trans-1-methyl-1-(4-pyridylcarbamoyl)cyclohexane
(103) trans-4-benzylaminomethyl-cis-2-methyl-1-(4-pyridylcarbamoyl)cyclohexane
(104) trans-4-(1-benzyloxycarboxamide-1-methylethyl)-1-(4-pyridylcarbamoyl)cyclohexane
(105) trans-4-benzyloxycarboxamidomethyl-1-(N-methyl-4-pyridylcarbamoyl)cyclohexane
(106) trans-4-(1-acetamide-1-methylethyl)-1-(4-pyridylcarbamoyl)cyclohexane
(107) trans-N-(6-amino-4-pyrimidyl)-4-aminomethylcyclohexanecarboxamide
(108) trans-N-(1H-pyrrolo[2,3-b]pyridin-4-yl)-4-aminomethylcyclohexanecarboxamide
(109) (+)-trans-N-(1H-pyrrolo[2,3-b]pyridin-4-yl)-4-(1-aminoethyl)cyclohexanecarboxamide
(110) trans-N-(1H-pyrrolo[2,3-b]pyridin-4-yl-4-(1-amino-1-methylethyl)cyclohexanecarboxamide
(111) trans-N-(1H-pyrazolo[3,4-b]pyridin-4-yl)-4-aminomethylcyclohexanecarboxamide
(112) (+)-trans-N-(1H-pyrazolo[3,4-b]pyridin-4-yl)-4-(1-aminoethyl)cyclohexanecarboxamide
(113) trans-N-(1H-pyrazolo[3,4-b]pyridin-4-yl)-4-(1-amino-1-methylethyl)cyclohexanecarboxamide
(114) (+)-trans-N-(2-amino-4-pyridyl)-4-(1-aminoethyl)cyclohexanecarboxamide
(115) trans-N-(1H-pyrazolo[3,4-d]pyrimidin-4-yl)-4-aminomethylcyclohexanecarboxamide (116) (+)-trans-N-(1H-pyrazolo[3,4-d]pyrimidin-4-yl)-4-(1-aminoethyl)cyclohexanecarboxamide
(117) trans-N-(1 H-pyrazolo[3,4-d]pyrimidin-4-yl)-4-(1-amino-1-methylethyl)cyclohexanecarboxamide
(118) trans-N-(4-pyrimidinyl)-4-aninomethylcyclohexanecarboxamide
(119) trans-N-(3-amino-4-pyridyl)-4-aminomethylcyclohexanecarboxamide
(120) trans-N-(7H-imidazo[4,5-d]pyrimidin-6-yl)-4-aminomethylcyclohexanecarboxamide
(121) trans-N-(3H-1,2,3-triazolo[4,5-]pyrimidin-7-yl)-4-aminomethylcyclohexanecarboxamide
(122) trans-N-(1-benzyl-1H-pyrazolo[3,4-b]pyridin-4-yl)-4-aminomethylcyclohexanecarboxamide
(123) trans-N-(1H-5-pyrazolyl)-4-aminomethylcyclohexanecarboxamide
(124) trans-N-(1H-pyrazolo[3,4-b]pyridin-4-yl)-4-aminomethylcyclohexanecarboxamide
(125) trans-N-(4-pyridazinyl)-4-aminomethylcyclohexanecarboxamide
(126) trans-N-(7H-pyrrolo[2,3-d]pyrimidin-4-yl)-4-aminomethylcyclohexanecarboxamide
(127) trans-N-(2-amino-4-pyridyl)-4-aminomethylcyclohexanecarboxamide
(128) trans-N-(thieno[2,3-d]pyrimidin-4-yl)-4-aminomethylcyclohexanecarboxamide
(129) trans-N-(5-methyl-1,2,4-triazolo[1,5-a]pyrimidin-7-yl)-4-aminomethylcyclohexanecarboxamide
(130) trans-N-(3-cyano-5-methylpyrazolo[1,5-a]pyrimidin-7-yl)-4-aminomethylcyclohexanecarboxamide
(131) trans-N-(1H-pyrazolo[3,4-b]pyridin-4-yl)-4-(1-amino-1-methylethyl)cyclohexanecarboxamide
(132) trans-N-(2-(1-pyrrolidinyl)-4-pyridyl)-4-aminomethylcyclohexanecarboxanide
(133) trans-N-(2,6-diamino-4-pyrimidyl)-4-aminomethylcyclohexanecarboxamide
(134) (+)-trans-N-(7-methyl-1,8-naphthyridin-4-yl)-4-(1-aminoethyl)cyclohexanecarboxamide
(135) trans-N-(1-benzyloxymethylpyrrolo[2,3-b]pyridin-4-yl)-4-aminomethylcyclohexanecarboxamide
(136) (+)-trans-N-(1-methylpyrrolo[2,3-b]pyridin-4-yl)-4-(1-aminoethyl)cyclohexanecarboxamide
(137) trans-N-benzyl-N-(2-benzylamino-4-pyridyl)-4-(1-amino-1-methylethyl)cyclohexanecarboxamide
(138) trans-N-(2-azide-4-pyridyl)-4-aminomethylcyclohexanecarboxamide
(139) trans-N-(2,3-dihydro-1H-pyrrolo[2,3-b]pryidin-4-yl)-4-aminomethylcylohexanecarboxamide
(140) trans-N-(2,3-dihydro-1H-pyrrolo[2,3-b]pyridin-4-yl)-4-(1-amino-1-methylethyl)cyclohexanecarboxamide
(141-1) trans-N-(2-carboxy-4-pyridyl)-4-aminomethylcyclohexanecarboxamide
(141-2) (R)-(+)-trans-N-(3-bromo-1H-pyrrolo[2,3-b]pyridin-4-yl)-4-(1-aminoethyl)cyclohexanecarboxamide
(142) trans-N-(1H-pyrrolo[2,3-b]pyridin-4-yl)-4-guanidinomethylcyclohexanecarboxamide
(143) trans-N-(1H-pyrazolo[3,4-b]pyridin-4-yl)-4-guanidinomethylcyclohexanecarboxamide
(144) trans-N-(4-pyridyl)-4-guanidinomethylcyclohexanecarboxamide
(145) trans-N-(1-methylpyrrolo[2,3-b]pyridin-4-yl)-4-(guanidinomethyl)cyclohexanecarboxamide
(146) trans-N-(1H-pyrrolo[2,3-b]pyridin-4-yl)-4-(2-imidazolin-2-yl)aminomethylcyclohexanecarboxamide
(147) trans-N-(1-benzyloxymethylpyrrolo[2,3-b]pyridin-4-yl)-4-guanidinomethylcyclohexanecarboxamide
(148) trans-N-(2-amino-4-pyridyl)-4-guanidinomethylcyclohexanecarboxamide
(149) trans-N-(1-benzyloxymethyl-1H-pyrrolo[2,3-b]pyridin-4-yl)-4-(2-imidazolin-2-yl)aminomethylcyclohexanecarboxamide
(150) trans-N-(1H-pyrrolo[2,3-b]pyridin-4-yl)-4-(3-benzylguanidinomethyl)cyclohexanecarboxamide
(151) trans-N-(1H-pyrrolo[2,3-b]pyridin-4-yl)-4-(3-phenylguanidinomethyl)cyclohexanecarboxamide
(152) trans-N-(1H-pyrrolo[2,3-b]pyridin-4-yl)-4-(3-propylguanidinomethyl)cyclohexanecarboxamide
(153) trans-N-(1H-pyr-rol[2,3-b]pyridin-4-yl)-4-(3-octylguanidinomethyl)cyclohexanecarboxamide
(154) trans-N-(1-benzyloxymethylprrolo[2,3-b]pyridin-4-yl)-4-(2-benzyl-3-ethylguanidinomethyl)cyclohexanecarboxamide
(155) trans-N-(1H-pyrrolo[2,3-b]pryidin-4-yl)-4-(imidazol-2-yl)aminomethylcyclohexanecarboxamide
(156) trans-N-(1H-pyrrolo[2,3-b]pryidin-4-yl)-4-(thiazol-2-yl)aminomethylcyclohexanecarboxamide
(157) (R)-(+)-N-(4-pyridyl)-4-(1-aminoethyl)benzamide
(158) N-(4-pyridyl)-4-(1-amino-1-methylethyl)benzamide
(159) N-(4-pyridyl)-4-aminomethyl-2-benzyloxybenzamide
(160) N-(4-pyridyl)-4-aminomethyl-2-ethoxybenzamide
(161) (R)-(−)-N-(4-pryidyl)-4-(1-aminoethyl)-3-nitrobenzamide
(162) (R)-(−)-N-(4-pyridyl)-3-amino-4-(1-arminoethyl)benzamide
(163) (R)-(+)-N-(4-pyridyl)-4-(1-aminoethyl)-3-chlorobenzamide
(164) N-(4-pyridyl)-3-aminomethylbenzamide
(165) (R)-(+)-N-(1H-pyrrolo[2,3-b]pyridin-4-yl)-4-(1-aminoethyl)benzaniide
(166) (R)-(+)-N-(1H-pyrazolo[3,4-b]pyridin4-yl)-4-(1-aminoethyl)benzamide
(167) N-(1H-pyrazolo[3,4-b]pyridin-4-yl-4-guanidinomethylbenzamide
(168) N-(4-pyridyl)-4-guanidinomethylbenzamide
(169) (R)-(+)-N-(4-pyridyl)4-(1-aminoethyl)-3-fluorobenzamide
(170) N-(4-pyridyl)-4-aminomethylbenzamide
(171) N-(4-pyridyl)-4-aminomethyl-2-hydryoxbenzamide
(172) N-(4-pyridyl)-1)-4-(2-aminoethyl)benzamide
(173) N-(4-pyridyl)-4-aminomethyl-3-nitrobenzamide
(174) N-(4-pyridyl)-3-amino-4-aminomethylbenzamide
(175) (S)-(−)-N-(4-pyridyl)-4-(1-arminoethyl)benzamide
(176) (S)-(−)-N-(4-pryidyl)-2-(1-arminoethyl)benzamide
(177) (R)-(+)-N-(4-pyridyl)-4-(1-aminoethyl)-2-chlorobenzamide
(178) (R)-(+)-N-(1H-pyrrolo[2,3-b]pyridin-4-yl)-4-(1-(3-propylguanidino)ethyl)benzarmide
(179) (R)-(−)-N-(1H-pyrrolo[2,3-b]pyridin-4-yl)-4-(1-aminoethyl)-3-azidebenzamide
(180) (R)-(+)-N-(4-pyridyl)-4-(1-aminoethyl)-2-nitrobenzamide
(181) (R)-(−)-N-(4-pyridyl)-4-(1-aminoethyl)-3-ethoxybenzamide
(182) (R)-(+)-N-(3-iodo-1H-pyrrolo[2,3-b]pyridin-4-yl)-4-(1-aminoethyl)benzamide
(183) (R)-(+)-N-(3-iodo-1H-pyrrolo[2,3-b]pyridin-4-yl)-4-(1-aminoethyl)-3-azidebenzamide
(184) (R)-(−)-N-(4-pyridyl)-4-(1-aminoethyl)-3-hydroxybenzamide
(185) N-(1H-pyrazolo[3,4-b]pyridin-4-yl)-4-guanidinomethyl-3-nitobenzamide
(186) (R)-N-(1H-pyrazolo[3,4-b]pyridin-4-yl)-4-(1-guanidinoethy-l)-3-nitrobenzamide
(187) (R)-N-(1H-pyrazolo[3,4-b]pyridin-4-yl)-4-(1-aminoethyl)-2-nitrobenzamide (188) N-(1H-pyrazolo[3,4-b]pyridin-4-yl)-4-guanidinobenzamide
(189) (R)-N-(1H-pyrazolo[3,4-b]pyridin-4-yl)-4-(1-aminoethyl)-3-nitrobenzamide
(190) (R)-N-(1H-pyrazolo[3,4-b]pyridin-4-yl)-4-(1-guanidinoethyl)benzamide
(191) N-(1H-pyrazolo[3,4-b]pyridin-4-yl)-4-(1-amino-2-hydroxyethyl)benzamide
(192) N-(1H-pyrazolo[3,4-b]pyridin-4-yl)-4-aminomethyl-3-nitrobenzamide
(193) N-(1H-pyrrolo[2,3-b]pyridin-4-yl)-4-piperidinecarboxamide
(194) N-(1H-pyrazolo[3,4-b]pyridin-4-yl)-4-piperidinecarboxamide
(195) N-(1H-pyrazolo[3,4-b]pyridin-4-yl)-1-aminoacetyl-4-piperidinecarboxamide
(196) N-(1-methoxymethyl-1H-pyrazolo[3,4-b]pyridin-4-yl)-4-piperidinecarboxamide
(197) N-(2,3-dihydro-1H-pyrrolo[2,3-b]pyridin-4-yl)-4-piperidinecarboxamide
(198) N-(1H-pyrrolo[2,3-b]pyridin-4-yl)-1-(2-phenylethyl)-4-pipeiidinecarboxamide
(199) N-(1H-pyrrolo[2,3-b]pyridin4-yl)-1-amidino-4-piperidinecarboxamide
(200) N-(1H-pyrrolo[2,3-b]pyridin-4-yl)-1-(3-phenylpropyl)-4-piperidinecarboxamide
(201) N-(1H-pyrrolo[2,3-b]pyridin-4-yl)-1-benzyl-4-piperidinecarboxanide
(202) N-(1H-pyrazolo[3,4-b]pyridin-4-yl)-1-(2-phenylethyl)-4-piperidinecarboxamide
(203) N-(1H-pyrazolo[3,4-b]pyridin-4-yl)-1-(3-phenylpropyl)-4-piperidinecarboxamide Preferred are compounds (80), (109), (110), (112), (115), (142), (143), (144), (145), (153), (157), (163), (165), (166) and (179).

The compound to be used as the Rho kinase inhibitor of the present invention is, for example, a compound of the formula (II), which is exemplified by the following compounds.
(204) 1-(5-isoquinolinesulfonyl)homopiperazine
(205) 1-(5-isoquinolinesulfonyl)-2-methylhomopiperaine
(206) 1-(5-isoquinolinesulfonyl)-3-methylhomopiperaine
(207) 1-(5-isoquinolinesulfonyl)-6-methylhomopiperazine
(208) 1-(5-isoquinolinesulfonyl)-2,3-dimethylhomopiperazine
(209) 1-(5-isoquinolinesulfonyl)-3,3-dimethylhomopiperazine
(210) 1-(5-isoquinolinesulfonyl)-3-ethylhomopiperazine
(211) 1-(5-isoquinolinesulfonyl)-3-propylhomopiperazine
(212) 1-(5-isoquinolinesulfonyl)-3-isobutylhomopiperazine
(213) 1-(5-isoquinolinesulfonyl)-3-phenylhomopiperazine
(214) 1-(5-isoquinolinesulfonyl)-3-benzylhomopiperazine
(215) 1-(5-isoquinolinesulfonyl)-6-ethylhomopiperazine
(216) 1-(5-isoquinolinesulfonyl)-6-propylhomopiperazine
(217) 1-(5-isoquinolinesulfonyl)-6-butylhomopiperazine
(218) 1-(5-isoquinolinesulfonyl)-6-pentylhomopiperazine
(219) 1-(5-isoquinolinesulfonyl)-6-hexlhomopiperzine
(220) 1-(5-isoquinolinesulfonyl)-6-phenylhomopiperazine
(221) 1-(5-isoquinolinesulfonyl)-6-benzylhomopiperazine
(222) 1-(5-isoquinolinesulfonyl)-4-methylhomopiperazine
(223) 1-(5-isoquinolinesulfonyl)-4-ethylhomopiperazine
(224) 1-(5-isoquinolinesulfonyl)-4-propylhomopiperazine
(225) 1-(5-isoquinolinesulfonyl)-4-butylhomopiperazine
(226) 1-(5-isoquinolinesulfonyl)-4-hexylhomopiperazine
(227) N-(2-aminoethyl)-1-chloro-5-isoquinolinesulfonamide
(228) N-(4-aminoethyl)-1-chloro-5-isoquinolinesulfonamide
(229) N-(2-amino-1-methylethyl)-1-chloro-5-isoquinolinesulfonamide
(230) N-(2-amino-1-methylpentyl)-1-chloro-5-isoquinoline
(231) N-(3-amino-2-methylbutyl)-1-chloro-5-isoquinolinesulfonamide
(232) N-(3-di-n-butyammopropyl)-1-chloro-5-isoquinolinesulfonamide
(233) N-(N-cyclohexyl-N-methylaminoethyl)-1-chloro-5-isoquinolinesulfonamide
(234) N-(2-guanidinoethyl)-1-chloro-5-isoquinolinesulfonamide
(235) N-(2-guanidinobutyl)-1-chloro-5-isoquinolinesulfonamide
(236) N-(2-guanidino-1-methylethyl)-1-chloro-5-isoquinolinesulfonamide
(237) N-(2-guanidinomethylpentyl)-1-chloro-5-isoquinolinesulfonamide
(238) N-(2-guanidino-3-methylbutyl)-1-chloro-5-isoquinolinesulfonamide
(239) N-(3-guanidino-2-methylpropyl)-1-chloro-5-isoquinolinesulfonamide
(240) N-(4-guanidino-3-methylbutyl)-1-chloro-5-isoquinolinesulfonamide
(241) 2-methyl-4-(1-chloro-5-isoquinolinesulfonyl)piperazine
(242) 2-ethyl-4-(1-chloro-5-isoquinolinesulfonyl)piperazine
(243) 2-isobutyl-4-(1-chloro-5-isoquinolinesulfonyl)piperazine
(244) 2,5-dimethyl-4-(1-chloro-5-isoquinolinesulfonyl)piperazine
(245) 1-methyl-4-(1-chloro-5-isoquinolinesulfonyl)piperazine
(246) 1-amidino-4-(1-chloro-5-isoquinolinesulfonyl)piperazine
(247) 1-amidino-4-(1-chloro-5-isoquinolinesulfonyl)homopiperazine
(248) 1-amidino-3-methyl4-(1-chloro-5-isoquinolinesulfonyl)piperaine
(249) 1-amidino-2,5-dimethyl-4-(1-chloro-5-isoquinolinesulfonyl)piperazine
(250) N-(2-aminoethyl)-1-hydroxy-5-isoquinolinesulfonamide
(251) N-(4-aminobutyl)-1-hydroxy-5-isoquinolinesulfonamide
(252) N-(2-amino-1-methylethyl)-1-hydroxy-5-isoquinolinesulfonamide
(253) N-(2-amino-1-methylheptyl)-1-hydroxy-5-isoquinolinesulfonamide
(254) N-(3-amino-2-methylbutyl)-1-hydroxy-5-isoquinolinesulfonamide
(255) N-[3-(N,N-dibutylamino)propyl]-1-hydroxy-5-isoquinolinesulfonamide
(256) N-[2-(N-cyclohexyl-N-methylamino)ethyl]-1-hydroxy-5-isoquinolinesulfonamide
(257) N-(2-guanidinoethyl)-1-hydroxy-5-isoquinolinesulfonamide
(258) N-(4-guanidinobutyl)-1-hydroxy-5-isoquinolinesulfonamide
(259) N-(2-guanidino-11-methylethyl)-1-hydroxy-5-isoquinolinesulfonamide
(260) N-(1-guanidinomethylpentyl)-1-hydroxy-5-isoquinolinesulfonamide
(261) N-(2-guanidino-3-methylbutyl)-1-hydroxy-5-isoquinolinesulfonamide
(262) N-(3-guanidino-2-methylpropyl)-1-hydroxy-5-isoquinolinesulfonamide
(263) N-(4-guanidino-3-methylbutyl)-1-hydroxy-5-isoquinolinesulfonaniide (264) 2-methyl-4-(1-hydroxy-5-isoquinolhnesulfonyl)piperazine
(265) 2-ethyl-4-(1-hydroxy-5-isoquinolinesulfonyl)piperzine
(266) 2-isobutyl-4-(1-hydroxy-5-isoquinolinesulfonyl)piperazine
(267) 2,5-dimethyl-4-(1-hydroxy-5-isoquinolinesulfonyl)piperazine
(268) 1-methyl-4-(1-hydroxy-5-isoquinolinesulfonyl)piperazine
(269) 1-amidino-4-(1-hydroxy-5-isoquinolinesulfonyl)piperazine
(270) 1-amidino-4-(1-hydroxy-5-isoquinolinesulfonyl)homopiperazine
(271) 1-amidino-3-methyl-(1-hydroxy-5-isoquinolinesulfonyl)piperazine
(272) 1-amidino-2,5-dimethyl-4-(1-hydroxy-5-isoquinolinesulfonyl)piperazine
(273) N-(2-methylamninoethyl)-1-chloro-5-isoquinolinesulfonamide
(274) N-(2-ethylaminoethyl)-1-chloro-5-isoquinolinesulfonamide
(275) N-(2-propylaminoethyl)-1-chloro-5-isoquinolinesulfonamide
(276) N-(2-butylaminoethyl)-1-chloro-5-isoquinolinesulfonamide
(277) N-(2-hexylamioethyl)-1-chloro-5-isoquinohinesulfonamide
(278) 1-(1-chloro-5-isoquinolinesulfonyl)piperazine
(279) 1-(1-chloro-5-isoquinolinesulfonyl)homopiperazine
(280) N-(2-methylaminoethyl)-1-hydroxy-5-isoquinolinesulfonamide
(281) N-(2-ethylaminoethyl)-1-hydroxy-5-isoquinolinesulfonamide
(282) N-(2-propylaminoethyl)-1-hydroxy-5-isoquinolinesulfonamide
(283) N-(2-butylaminoethyl)-1-hydroxy-5-isoquinolinesulfonamide
(284) N-(2-hexylaminoethyl)-1-hydroxy-5-isoquinolinesulfonamide
(285) 1-(1-hydroxy-5-isoquinolinesulfonyl)piperazine
(286) 1-(1-hydroxy-5-isoquinolinesulfonyl)homopiperazine
(287) 1-(5-isoquinolinesulfonyl)-4-methylpiperazine
(288) 1-(5-isoquinolinesulfonyl)-4-n-hexylpiperazine
(289) 1-(5-isoquinolinesulfonyl)-4-cinnamylpiperazne
(290) 1-(5-isoquinolinesulfonyl)piperazine
(291) N-(2-aminoethyl)-5-isoquinolinesulfonamide
(292) N-(4-aminobutyl)-5-isoquinolinesulfonamide
(293) N-(3-di-n-butylaminopropyl)-5-isoquinolinesulfonamide
(294) 1-(5-isoquinolinesulfonyl)-3-methylpiperazine
(295) 1-(5-isoquinolinesulfonyl)-3-isobutylpiperazine
(296) 1-(5-isoquinolinesulfonyl)-2,5-dimethylpiperazine
(297) N-(3-guanidino-2-phenylpropyl)-5-isoquinolinesulfonamide
(298) N-(6-guanidino-1-methylheptyl)-5-isoquinolinesulfonamide
(299) 2-[2-(5-isoquinolinesulfonamide)ethylamino]-2-imidazoline
(300) 2-amidino-1-(5-isoquinolinesulfonyl)piperazine
(301) 4-amidino-2,5-dimethyl-1-(5-isoquinolinesulfonyl)piperazine
(302) 4-amidino-1-(5-isoquinolinesulfonyl)homopiperazine
(303) 4-(N1,N2-dimethylamidino)-1-(5-isoquinolinesulfonyl)piperazine
(304) 4-amidino-3-butyl-1-(5-isoquinolinesulfonyl)piperazine
(305) 4-hexyl-1-(5-isoquinolinesulfonyl)ethylenediamine
(306) N-(4-guanidinobutyl)-5-isoquinolinesulfonamide
(307) N-(2-guanidinoethyl)-5-isoquinolinesulfonamide
(308) 1-(5-isoquinolinesulfonyl)-2-methylpiperazine Preferred are compounds (204) and (308).

The compound to be used as the Rho Idnase inhibitor of the present invention may be a pharmaceutically acceptable acid addition salt. The acid is exemplified by inorganic acid such as hydrochloric acid, hydrobromic acid, sulfuric acid and the like and organic acid such as methanesulfonic acid, fumaric acid, maleic acid, mandelic acid, citric acid, tartaric acid, salicylic acid and the like. The compound having a carboxyl group can be converted to a salt with a metal such as sodium, potassium, calcium, magnesium, aluminum and the like or a salt with amino acid such as lysine and the like. In addition, their monohydrate, dihydrates, 1/2 hydrates, 1/3 hydrates, 1/4 hydrates, 2/3 hydrates, 3/2 hydrates and the like are also encompassed in the present invention.

The compound of the formula (I) can be synthesized according to the method disclosed in Japanese Patent Unexamined Publication No. 62-89679, Japanese Patent Unexamined Publication No.3-218356, Japanese Patent Unexamined Publication No. 5-194401, Japanese Patent Unexamined Publication No. 6-41080, WO95/28387 and the like.

The compound of the formula (II) can be synthesized according to the method disclosed in Japanese Patent Unexamined Publication No. 57-156463, Japanese Patent Unexamined Publication No. 57-200366, Japanese Patent Unexamined Publication No. 58-121278, Japanese Patent Unexamined Publication No. 58-121279, Japanese Patent Unexamined Publication No. 59-93054, Japanese Patent Unexamined Publication No. 60-81168, Japanese Patent Unexamined Publication No. 61-152658, Japanese Patent Unexamined Publication No. 61-227581, Japanese Patent Unexamined Publication No. 62-103066, U.S. Pat. No. 4,678,783 and the like.

Of the compounds of the formula (I), a compound wherein Ra is a group of the formula (c) and Rc is Rc', namely, an amide compound of the formula (III):

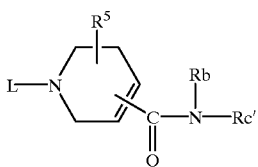

[III]

wherein Rc' is an optionally substituted heterocycle containing nitrogen of the above-mentioned Rc except pyridine, and other symbols are as defined above, is a novel compound which can be synthesized by the following methods.

Method 1

A compound of the formula (IV):

Rc'—NH—Rb    (IV)

wherein each symbol is as defined above, and a compound of the formula (V):

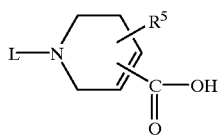

(V)

wherein each symbol is as defined above, or a reactive derivative thereof are reacted to give the compound. The reactive derivative of carboxylic acid compound is exemplified by acid halide, ester, acid anhydride, mixed acid anhydride and the like.

This reaction beneficially proceeds by stirring in the presence of a solvent inert to the reaction, such as tetrahydrofuran, dioxane, chloroform, dichloromethane, dimethylformamide, benzene, toluene, ethanol and the like. Water, alcohol or acid liberated during the reaction is removed from the reaction mixture by a method known in the pertinent field, such as azeotropic distillation, forming a complex, converting to salt and the like.

Method 2

Of the compounds of the formula (III), a compound wherein L has a substituent other than hydrogen can be produced by reacting a compound wherein L is hydrogen, with a compound of the formula (VI):

(VI)

wherein $L^1$ is, of the aforementioned L, a substituent other than hydrogen and M is a reactive atom, according to N-alkylation or N-acylation known in this field.

Method 3

Of the compounds of the formula (III), a compound wherein L is alkyl or has a substituent having the formula (i) can be produced by reductive amination reaction of a compound wherein L is hydrogen and a compound of the formula (VII):

(VII)

wherein $L^2$ is a group that can be converted to alkyl or a group of the formula (i), by reductive amination reaction.

Method 4

Of the compounds of the formula (III), a compound wherein L is a group of the formula (1):

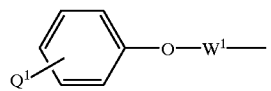

(1)

wherein $Q^1$ is as defined above and $W^1$ is hydroxytrimethylene from among the substituents at W, can be produced by reacting a compound of the formula (III)
wherein L is hydrogen and a compound of the formula (VIII):

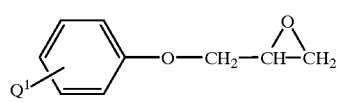

(VIII)

wherein $Q^1$ is as defined above.

The reaction advantageously proceeds in a suitable solvent which does not influence the reaction, such as alcohol (e.g., methanol, ethanol, 2-propanol and the like), aliphatic or alicyclic ketone (e.g., 2-propanone, 2-butanone, cyclohexane and the like) and the like. Addition of a suitable base such as alkali metal carbonate, hydrogencarbonate and the like enables acceleration of the reaction rate. The reaction temperature is rather elevating, which is preferably refluding temperature of the reaction mixture.

Method 5

Of the compounds of the formula (III), a compound wherein L is hydrogen can be produced from a compound of the formula (III-a):

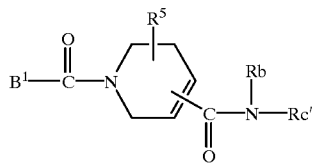

(III-a)

wherein $B^1$ is alkoxy or amikyloxy, from among the aforementioned substituents B, and other symbols are as defined above.

Of the compounds (III-a), a compound wherein $B^1$ is alkoxy is stirred in a suitable organic solvent which does not influence the reaction, such as alcohol (e.g., methanol, ethanol, 2-propanol and the like) and ether (e.g., tetrahydrofuran and the like) in the presence of a suitable base, such as hydroxide of alkali metal or alkaine earth metal, carbonate or hydrogencarbonate (e.g., sodium hydroxide, potassium carbonate, sodium hydrogencarbonate and the like) and heated as necessary to give a compound of the formula (III) wherein L is hydrogen.

Of the compounds (III-a), a compound wherein $B^1$ is aralkyloxy is subjected to reductive decomposition reaction in a suitable organic solvent which does not influence the reaction in the presence of a suitable catalyst such as palladium carbon and the like using a hydrogen source of hydrogen, hydra e, formic acid, ammonium formate and the like at normal temperature or under pressurization where necessary.

Moreover, a compound (III-a) is stirred in 5–35%, preferably 15–30, acetic acid in the presence of hydrogen bromide, whereby the compound can be converted. A compound of the formula (III-b):

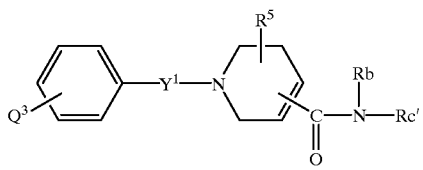

(III-b)

wherein $Y^1$ is methylene, from among the aforementioned substituents Y, and other symbols are as defined above, is subjected to catalytic hydrogenation decomposition reaction wherein the compound is stirred in a suitable organic solvent which does not influence the reaction in the presence of a suitable catalyst such as palladium carbon and the like under hydrogen to give a compound of the formula (III) wherein L is hydrogen.

The compound of the formula (III) thus obtained can be separated from the reaction mixture and purified by a method known in the field of art, such as recrystallization, chromatography and the like.

In addition, the compound of the formula (III) can form a pharmaceutically acceptable salt by a conventional method. The acid to be used for forming a salt can be appropriately selected from inorganic acids such as hydrochloric acid, hydrobromic acid, sulfuric acid and the like, organic acids such as methanesulfonic acid, fumaric acid, maleic acid, mandelic acid, citric acid, tartaric acid, salicylic acid and the like, amino acids such as lysine and the like, and metal such as sodium, potassium, calcium, magnesium, aluminum and the like. These acid addition salts can be converted to a corresponding free base by the reaction with alkl such as sodium hydroxide, potassium hydroxide and the like according to a known method. The salts can be also converted to quaternary ammonium.

The compound of the formula (III) may exist as optical isomer, racemate thereof or cis-trans isomer, all of which are encompassed in the present invention. These isomers can be isolated by a conventional method or produced by using various starting compounds.

When the Rho kinase inhibitor of the present invention is used as a pharmaceutical agent, particularly as a therapeutic agent of hypertension, a therapeutic agent of angina pectoris, a suppressive agent of cerebrovascular contraction, a therapeutic agent of asthma, a therapeutic agent of peripheral circulation disorder, a prophylactic agent of immature birth, a therapeutic agent of arteriosclerosis, an anti-cancer drug, an anti-inflammatory agent, an immunosuppressant, a therapeutic agent of autoimmune disease, a contraceptive, a prophylactic agent of digestive tract infection, an anti-AIDS drug, a therapeutic agent of osteoporosis, a therapeutic agent of retinopathy or a brain function improving drug, it can be prepared as a general pharmaceutical agent. For example, the Rho kinase inhibitor of the present invention is mixed with a pharmaceutically acceptable carrier (e.g., excipient, binder, disintegrator, corrective, corrigent, emulsifier, diluent, solubilizer and the like) to give a pharmaceutical composition or a pharmaceutical preparation in the form of tablet, pill, powder, granule, capsule, troche, syrup, liquid, emulsion, suspension, injection (e.g., liquid, suspension and the like), suppository, inhalant, percutaneous absorber, eye drop, eye ointment and the like in the form suitable for oral or parenteral preparation.

When preparing a solid preparation, an additive such as sucrose, lactose, cellulose sugar, D-mannitol, maltitol, dextan, starches, agar, arginates, chitins, chitosans, pectines, tragacanth, gum arabic, gelatins, collagens, casein, albumin, calcium phosphate, sorbitol, glycine, carboxymethyl cellulose, polyvinylpyrrolidone, hydroxypropylcellulose, hydroxypropylmethylcellulose, glycerol, polyethyleneglycol, sodium hydrogencarbonate, magnesium stearate, talc and the like are used. Tablets can be applied with a typical coating, where necessary, to give sugar coated tablets, enteric tablets, film-coated tablets, two-layer tablets and multi-layer tablets.

When preparing a semi-solid preparation, animal and plant fats and oils (e.g., olive oil, corn oil, castor oil and the like), mineral fats and oils (e.g., petrolatum, white petrolatum, solid parain and the like), wax (e.g., jojoba oil, carnauba wax, bee wax and the like), partly or entirely synthesized glycerol fatty acid esters (e.g., lauric acid, myristic acid, palnitic acid and the like), and the like are used. Examples of commercially available products of these include Witepsol (manufactured by Dynamitnovel Ltd.), Farmazol (NOF Corporation) and the like.

When preparing a liquid preparation, an additive, such as sodium chloride, glucose, sorbitol, glycerol, olive oil, propylene glycol, ethyl alcohol and the like, is used. In particular, when preparing an injection, a sterile aqueous solution such as physiological saline, isotonizing liquid, oily liquid (e.g., sesame oil and soybean oil) and the like is used. Where necessary, a suitable suspending agent such as sodium carboxymethylcellulose, nonionic surfactant, solubilizer (e.g., benzyl benzoate and benzyl alcohol), and the like can be concurrently used. Moreover, when an eye drop is prepared, an aqueous liquid or solution is used, which is particularly a sterile injectable aqueous solution. The liquid for an eye drop can appropriately contain various additives such as buffer (preferred are borate buffer, acetate buffer, carbonate buffer and the like for less irritation), isotonizing agent, solubilizer, preservative, thickener, chelating agent, pH adjuster (preferably, pH is generally adjusted to about 6–8.5) and aromatic.

The content of the active ingredient in these preparation is 0.1–100 wt %, suitably 1–50 wt %, of the preparation. While subject to variation depending on the condition, body weight, age and the like of patient, in general, about 1–500 mg of the active ingredient is orally administered daily for an adult in a single dose or several doses.

EXAMPLES

The present invention is described in more detail in the following by way of Examples, Formulation Examples and pharmacological action, to which the present invention is not limited.

In the following, the synthetic method of the novel compound of the formula (III) of the present invention is described by referring to examples.

Example 1

(a) N-Benzyloxycarbonylisonipecotyl chloride (5 g) was added to a solution of 4-amino-1-tert-butoxycarbonyl-1H-pyrrolo[2,3-b]pyridine (3 g) and diisopropylethyamine (2.16 g) in acetonitrile (40 ml) and the mixture was stirred at room temperature for 2 hours. The reaction mixture was poured into ice-water and extracted with chloroform. The residue obtained by water washing, drying and then concentration under reduced pressure was purified by silica gel column chromatography to give 6.3 g of N-(1-tert-butoxycarbonyl-1H-pyrrolo-[2,3-b]pyridin-4-yl)-1-benzyloxycarbonyl-4-piperidinecarboxamide.

PMR(CDCl$_3$): 1.67(9H, s), 1.79(2H, m), 1.95(2H, m), 2.53(1H, m), 2.89(2H, m), 4.29(2H, m), 5.15(2H, s), 6.48 (1H, d,J=4.4 Hz), 7.36(5H, m), 7.59(1H, br), d,J=4.4 Hz), 7.99(1H, d,J=5.4 Hz), 8.43(1H, d,J=5.4 Hz)

(b) N-(1-tert-Butoxycarbonyl-1H-pyrrolo[2,3-b]pyridin-4-yl)-1-benzyloxycarbonyl-4-piperidinecarboxamide (2 g) was dissolved in methanol (30 ml) and 10% palladium carbon hydroxide (0.5 g) was added for hydrogenation (normal pressure). After the completion of the reaction, the catalyst was filtered off and the filtrate was concentrated under reduced pressure to give 1.2 g of N-(1-tert-butoxycarbonyl-1H-pyrrolo[2,3-b]pyridin-4-yl)-4-piperidinecarboxamide.

PMR(DMSO-d$_6$): 1.59(9H, s), 1.83(2H, m), 2.01(2H, m), 2.89(2H, m), 3.01(1H, m), 3.32 (2H, m), 7.19(1H, d,J=4.4 Hz), 7.68(1H, d,J=4.4 Hz), 7.97(1H, d,J=5.4 Hz), 8.24(1H, d,J=5.4 Hz), 8.81(1H, br), 10.45(1H, s)

(c) Formic acid (10 ml) was added to N-(1-tert-butoxycarbonyl-1H-pyrrolo[2,3-b]pyridin-4-yl)4-piperidinecarboxamide (1 g) and the mixture was stirred at room temperature for 2 hours. The mixture was neutralized with aqueous 1N sodium hydroxide solution and extracted with chloroform. The crystals obtained by water washing, drying and then concentration under reduced pressure were dissolved in 15% hydrochloric acid-methanol solution (5 ml). The crystals obtained by concentration of the resulting solution were recrystallized from ethanol-ethyl acetate to give 650 mg of N-(1H-pyrrolo[2,3-b]pyridin-4-yl)-4-piperidinecarboxamide mono hydrochloride monohydrate, melting point 273° C. (decomposition).

PMR(DMSO-d$_6$): 1.52(2H, m), 1.69(2H, m), 2.51(2H, m), 2.70(1H, m), 2.97(2H, m), 3.32(1H, br), 6.79(1H, d,J=3.4 Hz), 7.31(1H, d,J=3.4 Hz), 7.79(1H, d,J=5.4 Hz), 8.04 (1H, d,J=5.4 Hz), 9.82(1H, s), 11.54(1H, br)

Example 2

(a) A solution of N-(1-tert-butoxycarbonyl-1H-pyrrolo[2,3-b]pyridin-4-yl)-4-piperidinecarboxamide (0.6 g), phenetyl bromide (390 mg) and potassium carbonate (290 mg) in dimethylfornamide (10 ml) was stirred at 80° C. for 2 hours. The reaction mixture was poured into ice water and extracted with chloroform. The residue obtained by water washing, drying and then concentration under reduced pressure was purified by silica gel column chromatography to give 550 mg of N-(1-tert-butoxycarbonyl-1H-pyrrolo[2,3-b]pyridin-4-yl)-1-(2-phenylethyl)-4-piperidinecarboxamide.

PMR(DMSO-d$_6$): 1.59(9H, s), 1.66(2H, m), 1.80(2H, m), 1.98(2H, m), 2.50(2H, m), 2.56(1H, m), 2.74(2H, m), 3.01 (2H, m), 7.05(1H, d,J=4.4 Hz), 7.23(5H, m), 7.68(1H, d,J=4.4 Hz), 7.97(1H,J=5.4 Hz), 8.23(1H, d,J=5.4 Hz), 10.03(1H, s)

(b) Formic acid (5 ml) was added to N-(1-tert-butoxycarbonyl-1H-pyrrolo[2,3-b]pyridin-4-yl)-1-(2-phenylethyl)-4-piperidinecarboxamide (550 mg) and the mixture was stirred at room temperature for 2 hours. The mixture was neutralized with aqueous 1N sodium hydroxide solution and extracted with chloroform. The crystals obtained by water washing, drying and then concentration under reduced pressure were dissolved in 15% hydrochloric acid-methanol solution (1 ml). The crystals obtained by concentration of the resulting solution were recrystallized from ethanol-ethyl acetate to give 250 mg of N-(1H-pyrrolo[2,3-b]pyridin-4-yl)-1-(2-phenylethyl)-4-piperidinecarboxamide dihydrochloride 1/4 hydrate, melting point 272° C. (decomposition).

PMR(DMSO-d$_6$/TMS) : 2.00–2.19(4H, m), 2.93–3.41 (7H, m), 3.63–3.68(2H, m), 7.22–7.37(5H, m), 7.50(1H, d,J=2.0 Hz), 7.56(1H, t,J=2.0 Hz), 8.25(1H, d,J=6.8 Hz), 8.33(1H, d,J=6.8 Hz), 10.86(1H, br), 11.36(1H, s), 12.77 (1H, br)

Example 3

(a) A solution of N-(1-tert-butoxycarbonyl-1H-pyrrolo[2,3-b]pyridin-4-yl)-4-piperidinecarboxamide (500 mg), benzyl bromide (370 mg) and potassium carbonate (300 mg) in dimethylformamide (10 ml) was stirred at 80° C. for 4 hours. The reaction mixture was poured into ice-water and extracted with chloroform. The residue obtained by water washing, drying and then concentration under reduced pressure was purified by silica gel column chromatography to give 300 mg of N-(1-tert-butoxycarbonyl-1H-pyrrolo[2,3-b]pyridin-4-yl)-1-benzyl-4-piperidinecarboxamide.

PMR(CDCl$_3$): 1.65(9H, s), 1.91(4H, m), 2.04(2H, m), 2.35(1H, m), 2.97(2H, m), 3.51(2H, s), 6.44(1H, d,J=3.9 Hz), 7.30(5H, m), 7.49(1H, br), 7.57(1H, d,J=3.9 Hz), 7.99(1H, d,J=5.4 Hz), 8.41(1H, d,J=5.4 Hz)

(b) Formic acid (4 ml) was added to N-(1-tert-butoxycarbonyl-1H-pyrrolo[2,3-b]pyridin-4-yl)-1-benzyl-4-piperidinecarboxamide (300 mg) and the mixture was stirred at room temperature for 1 hour. The mixture was neutralized with aqueous 1N sodium hydroxide solution and extracted with chloroform. The crystals obtained by water washing, diying and then concentration under reduced pressure were dissolved in 15% hydrochloric acid-methanol solution (1 ml). The crystals obtained by concentration of the resulting solution were recrystallized from ethanol-ethyl acetate to give 120 mg of N-(1H-pyrrolo[2,3-b]pyridin-4-yl)-1-benzyl-4-piperidinecarboxamide dihydrochloride monohydrate, melting point 260° C. (decomposition).

PMR(DMSO-d$_6$/TMS) : 2.00–2.15(4H, m), 2.92–2.98 (2H, m), 3.13–3.19(1 H, m), 3.36–3.43(2H, m), 4.32(2H, s), 7.55(1H, br), 7.63(2H, m), 8.20(1H, d,J=6.4 Hz), 8.31(1H, d,J=6.4 Hz), 10.76(1H, br), 11.25(1H, br), 12.69(1H, br)

The following compounds can be obtained in the same manner as in the above Examples.

Example 4

N-(1H-pyrazolo[3,4-b]pyridin-4-yl)-4-piperidinecarboxamide dihydrochloride 3/2 hydrate, melting point 277° C. (decomposition)

Example 5

N-(1 H-pyrazolo[3,4-b]pyridin-4-yl)-1-aminoacetyl-4-piperidinecarboxamide dihydrochloride 1/2 hydrate, melting point 264° C. (decomposition)

Example 6

N-(1-methoxymethyl-1H-pyrazolo[3,4-b]pyridin-4-yl)-4-piperidinecarboxamide monohydrate, melting point 240–241° C.

Example 7

N-(2,3-dihydro-1H-pyrrolo[2,3-b]pyridin-4-yl)-4-piperidinecarboxamide dihydrochloride 3/2 hydrate, melting point 235° C. (decomposition)

Example 8

N-(1H-pyrrolo[2,3-b]pyridin-4-yl)-1-amidino-4-piperidinecarboxamide dihydrochloride 5/4 hydrate, melting point 246° C. (decomposition)

Example 9

N-(1H-pyrrolo[2,3-b]pyridin4-yl)-1-(3-phenylpropyl)-4-piperidinecarboxamide dihydrochloride, melting point 276° C. (decomposition)

Example 10

N-(1H-pyrazolo[3,4-b]pyridin-4-yl)-1-(2-phenylethyl)-4-piperidinecarboxamide dihydrochloride hydrate, melting point 259–261° C. (decomposition)

Example 11

N-(1H-pyrazolo[3,4-b]pyridin-4-yl)-1-(3-phenylpropyl)-4-piperidinecarboxamide dihydrochloride 1/2 hydrate, melting point 240–244° C. (decomposition)

A method for preparing the pharmaceutical preparation of the present invention is explained in the following.

Formulation Example 1: Tablets

| | |
|---|---|
| Inventive compound | 10.0 mg |
| Lactose | 50.0 mg |
| Corn starch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The inventive compound, lactose, corn starch and crystalline cellulose were mixed, kneaded with polyvinylpyrrolidone K30 paste solution and passed through a 20-mesh sieve for granulation. After drying at 50° C. for 2 hours, the granules were passed through a 24-mesh sieve, and talc and magnesium stearate were added. Using a φ7 mm punch, tablets weighing 120 mg per tablet were prepared.

Formulation Example 2: Capsules

| | |
|---|---|
| Inventive compound | 10.0 mg |
| Lactose | 70.0 mg |
| Corn starch | 35.0 mg |
| Polyvinylpyrrolidone K30 | 2.0 mg |
| Talc | 2.7 mg |
| Magnesium stearate | 0.3 mg |
| | 120.0 mg |

The inventive compound, lactose, corn starch and crystalline cellulose were mixed, kneaded with polyvinylpyrrolidone K30 paste solution and passed through a 20-mesh sieve for granulation. After drying at 50° C. for 2 hours, the granules were passed through a 24-mesh sieve and talc and magnesium stearate were added. The mixture was filled in hard capsules (No. 4) to give capsules weighing 120 mg.

The pharmacological action of the pharmaceutical preparation of the present invention is explained in the following by way of experimental examples.

Experimental Example 1 : Rho Kinase Inhibitory Action (Inhibition of Bovine Aorta Thoracia Rho Kinase)

The Rho kinase was prepared from bovine aorta of thorax by partial purification as in the following. The artery was minced and homogenized with a 9-fold amount of 50 mM Tris-hydroxymethylaminomethane (Tris) (pH=7.4), 1 mM dithiothreitol, 1 mM EGTA, 1 mM EDTA, 100 μM p-amidinophenylmethylsulfonyl fluoride, 5 μM E-64, 5 μM leupeptine and 5 μM pepstatin A. The homogenate was centrifuged (10,000×g, 30 minutes) to give supernatant. The supernatant was adsorbed onto a hydroxyapatite column. The column was washed with 0.2M phosphate buffer (pH=6.8). The standard product of Rho kinase was eluted with 0.4M phosphate buffer (pH=6.8). The Rho kinase was assayed as follows.

A reaction mixture (total amount 50 μl) containing 50 mM Tris, 1 mM EDTA, 5 mM $MgCl_2$, 50 μg/ml histone, 10 μM GTPγS, 100 μg/ml Rho, 2 μM [$^{32}$P]ATP, the Rho kinase (3 μl) prepared in the above and the test compound was reacted at 30° C. for 5 minutes. The reaction was terminated by the addition of 25% trichloroacetic acid (TCA) solution (1 ml) and the mixture was stood at 4° C. for 30 minutes. Then, the mixture was filtered through a membrane filter (HAWP type, Millipore), and the radioactivity of the filter was counted on a liquid scintillation counter. The inhibitory action of the test compound was calculated from the following formula based on the comparison of the radioactivity with the sample without the test compound (control). The results are shown in Table 1.

TABLE 1

$$\text{Inhibition}(\%) = \left( \frac{\text{cpm under control} - \text{cpm in the presence of test compound}}{\text{cpm under control}} \right) \times 100$$

| Test compound | | Inhibition (%) |
|---|---|---|
| Compound 109.2HCl | (1 μM) | 81 |
| | (10 μM) | 100 |
| Compound 165.2HCl.3/2H$_2$O | (10 μM) | 100 |
| Compound 80.2HCl.H$_2$O | (10 μM) | 100 |
| Compound 204.2HCl | (10 μM) | 93 |

Experimental Example 2: Rho Kinase Inhibitory Action (Inhibition of Human Platelet Rho Kinase (p160ROCK))

Human platelet p160ROCK was isolated by the method of Ishizaki et al. (Ishizaki T et al., The EMBO J., 15(8), 1885–1893, 1996).

Kinase assay included the following steps. That is, a reaction mixture (total amount 30 μl) containing 50 mM Hepes-NaOH (pH=7.4), 10 mM $MgCl_2$, 5 mM $MnCl_2$, 2 mM dithiothreitol, 0.02% Brij35, 1 μM [γ-$^{32}$P]ATP, 330 μg/ml histone, p160ROCK (2 μl) isolated by the method of Ishizaki et al. and the test compound was incubated at 30° C. for 20 minutes. The solution was mixed with a 1/3 amount of 4×Laemmli sample buffer, boiled for 5 minutes and applied to SDS-PAGE. The gel was stained with Coomassie Brilliant Blue and dried. The band of histone was cut out and assayed for radioactivity. The test compound was evaluated in the same manner as in Experimental Example 1, and the concentration of each test compound necessary for 50% inhibition was calculated as IC50 (μM). The results are shown in Table 2.

TABLE 2

| Test compound | IC$_{50}$ (μM) |
|---|---|
| Compound 80.2HCl.H$_2$O | 1.5 |
| Compound 109.2HCl | 0.11 |
| Compound 143.2HCl.H$_2$O | 1.6 |
| Compound 204.2HCl | 3.8 |
| Compound 308.2HCl | 5.0 |

Experimental Example 3: Rho Kinase Inhibitory Action (Inhibition of p160ROCK and ROCKII)

The standard enzyme products of p160ROCK (Ishizaki T et al., The EMBO J., 15(8), 1885–1893, 1996) and ROCKII (Nakagawa O et al., FEBS Lett. 392 189–193, 1996) were obtained in the following manner. COS cells were seeded in a 3.5 cm dish and incubated overnight. Using lipofectamine, the expression vectors of p160ROCK and ROCKI (pCAG-myc-p160ROCK and pCAG-myc-ROCKII: see Ishizaki T et al., The EMBO J., 15(8), 1885–1893, 1996 and Nakagawa O et al., FEBS Lett. 392 189–193, 1996) were transfected. After incubation for 20 hours, the cells were washed once with ice-cooled PBS, and the cells were lysed on ice for 20 minutes using a lysis buffer (20 mM Tris-HCl (pH=7.5), 1 mM EDTA, 1 mM EGTA, 5 mM $MgCl_2$, 25 mM NaF, 10 mM β glycerophosphate, 5 mM sodium pyrophorphate, 0.2 mM phenylmethylsulfonyl fluoride, 2 mM dithiothreitol, 0.2 mM sodium vanadate, 0.05% Triton X-100, 0.1 μM calyculin A). The lysate was centrifuged at 10,000×g for 10 minutes and the supernatant was recovered. To the supernatant was added 9E10 anti-myc epitope antibody (see Ishizald T et al., The EMBO J., 15(8), 1885–1893, 1996) and the mixture was shaken for 2 hours. Then, protein G-Sepharose was added and the mixture was shaken for 2 more hours. The suspension was centrifuged at 1,000×g for 5 minutes and the resulting pellets were washed 3 times with lysis buffer and once with kinase buffer (50 mM Hepes-NaOH (pH=7.4), 10 mM $MgCl_2$, 5 mM $MnCl_2$, 2 mM dithiothreitol, 0.02% Brij35). The pellets were suspended in kinase buffer to give a standard enzyme product. The kinase assay followed the method shown in Experimental Example 2, wherein the standard enzyme product obtained in this Experimental Example was used instead of human platelet Rho kinase (p160ROCK). The concentration of each test compound necessary for 50% inhibition was calculated as IC50 (μM). The results are shown in Table 3.

TABLE 3

| | IC$_{50}$ (μM) | |
|---|---|---|
| Test compound | p160ROCK | ROCK-II |
| Compound 80.2HCl.H$_2$O | 0.63 | 0.56 |
| Compound 109.2HCl | 0.095 | 0.048 |

TABLE 3-continued

| Test compound | IC$_{50}$ ($\mu$M) | |
|---|---|---|
| | p160ROCK | ROCK-II |
| Compound 143.2HCl.H$_2$O | 0.88 | 0.47 |
| Compound 204.2HCl | 2.3 | 1.1 |

Experimental Example 4: Vasodilating Action

Male rabbits (body weight 1.9–3.0 kg) were anesthetized with pentobarbital sodium and exsanguinated, whereafter thoractic aorta was removed. An about 2 mm width aortic ring samples were prepared and hung in a Magnus bath (40 ml) filled with Krebs-Henseleit solution (37° C., NaCl 117 mM; KCl 4.7 mM; CaCl$_2$ 2.5 mM MgSO$_4$ 1.2 mM NaHCO$_3$ 24.8 mM KH$_2$PO$_4$ 1.2 mM glucose 11.0 mM) at a load of 2 g. The Magnus bath was constantly bubbled with a mixed gas (95% O$_2$+5% CO$_2$ gas). The tension of the preparation was measured with an isomeric transducer (TB-611T, Nippon Koden). The preparation was contracted with phenylephrine ($10_{-6}$ M) and, after the contraction was stabilized, the test compound was added accumulatively and relaxing action was observed. The relaxing action of the test compound was calculated by expressing the concentration of the test compound necessary for 50% relaxation as IC50 ($\mu$M) against the contraction with phenylephrine as 100%. The results are shown in Table 4.

Experimental Example 5: Effect on Contraction by Acetylcholine of Trachea Specimen Removed From Guinea Pig Male Hartley guinea pigs (body weight 260–390 g) were anesthetized by the peritoneal administration of pentobarbital sodium (100 mg/kg) and exsanguinated, whereafter trachea was removed. The anterior crtilage of the trachea was opened and the band was cut in a 3 mm width strip to give a specimen. The specimen was hung in a Magnus bath (40 ml) filled with Krebs-Henseleit solution (NaCl 117 mM; KCl 4.7 mM; CaCl$_2$ 2.5 mM; MgSO$_4$ 1.2 mM; NaHCO$_3$ 24.8 mM; KH2PO$_4$ 1.2 mM ; glucose 11.0 mM) at a load of 1 g. The Magnus bath was constantly bubbled with a mixed gas (95% O$_2$+5% CO$_2$ gas). The tension of the strip was measured with an isomeric transducer (TB-611T, Nippon Koden) and depicted on a recorder (Ti-102, Tokai Irika). The strip was contracted with acetylcholine ($10^{-6}$ M) and, after the contraction was stabilized, the test compound was added accumulatively and relaxing reaction was observed. The relaxing action of the test compound was calculated and expressed by the concentration of the test compound necessary for 50% relaxation as IC50 ($\mu$M) against the maximum response with papaverine ($10^{-4}$ M) as 100%. The results are shown in Table 4.

TABLE 4

| Test compound | Vasorelaxing action ($\mu$M) | Trachea relaxing action ($\mu$M) |
|---|---|---|
| Compound 80.2HCl.H$_2$O | 0.70 | 0.56 |
| Compound 109.2HCl | 0.1 | 0.043 |
| Compound 165.2HCl.3/2H$_2$O | 0.051 | 0.066 |
| Compound 179.2HBr.1/2H$_2$O | 0.03 | 0.029 |

Experimental Example 6: Peripheral Blood Flow Increasing Action

Streptozotocin (STZ, 65 mg/kg) was intravenously injected to male SD rats (body weight 200–300 g) to prepare diabetic rats. One month later, STZ-induced diabetic rats were anesthetized with pentobarbital sodium and the blood flow in the hind limb skin was measured with laser blood flowmeter (ALF21R, Advance). The test compound was intravenously administered via catheter dwelled in the carotid arteries, and hind limb slin blood flow increasing action was observed. The blood flow increasing action of the test compound was expressed by increase percentage from the blood flow before administration. The results are shown in Table 5.

TABLE 5

| Test compound | | Increase in skin blood flow ± standard error (%) |
|---|---|---|
| Compound 80.2HCl.H$_2$O | (1 $\mu$g) | 135.0 ± 13.4 |
| Compound 157.HCl.H$_2$O | (1 $\mu$g) | 211.6 ± 13.6 |
| Compound 165.2HCl.3/2H$_2$O | (0.03 $\mu$g) | 135.81 ± 0.0 |
| | (0.1 $\mu$g) | 144.7 ± 0.0 |
| Compound 166.2HCl.H$_2$O | (0.3 $\mu$g) | 143.2 ± 25.4 |
| | (1 $\mu$g) | 165.9 ± 42.5 |

Experimental Example 7: Inhibition of VIA (Very Late Antigen) Integrin Activation As the index of the activation by VLA integrin, phorbol ester-induced adhesion of CEM cells (human T cell type established cell) to fibronectin, which is a ligand of VLA integlin, was measured. The inhibitory action on the induced adhesion by the test compound was determined by the following method.

CEM cells were washed with RPMI1640 medium containing 0.5% bovine serum albumin (BSA), 10 mM HEPES, 2 mM L-glutamin, 1 mM sodium pyruvate, 60 $\mu$g/ml kanamycin sulfate and 1.5 mg/ml sodium hydrogencarbonate (hereinafter this medium is referred to as culture solution) and suspended in this medium for use in the following experiment. To each well of a 96 well plate coated with human fibronectin were added CEM cells ($5\times10^4$) and the test compound dissolved in the culture solution (final concentration 1–100 $\mu$M) to the amount of 100 $\mu$l, and the plate was stood at 37° C. for 1 hour. Then, PMA (phorbol 12-myristate 13-acetate, TPA; final concentration 10 ng/ml) and the test compound were added to the amount of 200 $\mu$l, and the plate was stood at 37° C. for 30 minutes. Each well was washed twice with the culture solution (200 $\mu$l) at 37° C., and the LDH (lactate dehydrogenase) activity of the cells adhered to the plate was determined, whereby the amount of the adhered cell was measured. Based on the results obtained by the above-mentioned method, the inhibitory action of the test compound on the induced adhesion was calculated by the following formula The results are shown in Table 6.

Inhibition (%) of adhesion induction=(a-b)/(a-c)×100 a=number of cells adhered with the addition of PMA b=number of cells adhered with the addition of test compound and PMA c=number of cells adhered without stimulation

TABLE 6

| Test compound | Concentration ($\mu$M) | Adhesion induction inhibition (%) |
|---|---|---|
| Compound 80.2HCl.H$_2$O | 100 | 70 |
| Compound 109.2HCl | 100 | 67 |
| Compound 143.2HCl.H$_2$O | 100 | 77 |
| Compound 165.2HCl.3/2H$_2$O | 10 | 40 |
| Compound 204.2HCl | 100 | 82 |

TABLE 6-continued

| Test compound | Concentration ($\mu$M) | Adhesion induction inhibition (%) |
|---|---|---|
| Anti-β1 antibody | 20 $\mu$g/ml | 118 |
| IgG1 | 20 $\mu$g/ml | −25 |

Experimental Example 8: Inhibition of Bone Resorption (in vitro)

The determination of the in vitro inhibition of bone resorption using mouse femoral bone followed the method below.

The femoral bone of 3–6 week old male ICR mice was aseptically removed, and bone marrow cavity was washed with F12 medium, containing 10% heat inactivated fetal bovine serum, penicillin G calcium (100 units/ml), kanamycin sulfate (60 $\mu$g) and 0.15% sodium hydrogencarbonate (hereinafter the medium is to be referred to as culture solution). After washing the bone marrow cavity and then removing the soft tissue adhered to the bone, the bone was subjected to incubation. The test compound was once dissolved in dimethyl sulfoxide (DMSO) to give a 10 mg/ml solution, which was diluted 1000-fold with the culture solution to give a 10 $\mu$g/ml solution. The test compounds were respectively added to the concentration shown in Table 7 and, using this culture solution (1.2 ml), the ICR mouse femoral bone was incubated in a 24 well plate for 6 days under the conditions of 5% $CO_2$ gas, 95% air. After the completion of the incubation, the culture supernatant was recovered, and the amount of calcium suspending in the culture supernatant was quantitatively determined by the chelate method using o-cresolphthalein. The bone resorption inhibitory action of the test compound was calculated by the following formula using the incubation of the femoral bone without addition of the test compound as a control.

$$\text{Inhibition of bone resorption (\%)} = \frac{\begin{pmatrix}\text{Amount of free } Ca \\ \text{without addition of} \\ \text{test compound}\end{pmatrix} - \begin{pmatrix}\text{amount of free } Ca \\ \text{with addition of} \\ \text{test compound}\end{pmatrix}}{\begin{pmatrix}\text{Amount of free } Ca \\ \text{without addition of} \\ \text{test compound}\end{pmatrix} - \begin{pmatrix}\text{Amount of } Ca \\ \text{in culture}\end{pmatrix}} \times 100$$

This experiment was done with 4 cases in each group. As the control, the same amount of DMSO alone as in the case with the addition of the test compound was used. The results are shown in Table 7.

Experimental Example 9: Inhibition of Mouse Allogenic Mixed Lymphocyte Reaction

A mouse allogenic mixed lymphocyte reaction (hereinafter to be referred to as mouse allogenic MLR) was performed by mixed culture (equal ratio) of the spleen cell of BALB/c mice as the reaction cell and the spleen cell of C57BL/6 mice treated with mitomycin C as stimulated cell.

The reaction cells were prepared by the following method. Spleen was removed from 5–6 week old BALB/c mice and treated with RPMI1640 medium (containing kanamycin sulfate (60 $\mu$g/ml), penicillin G potassium (100 units/ml), N-2-hydroxyethylpiperazine-N'-2-ethanesulfonate (10 mM), 0.1% sodium hydrogencarbonate and L-glutamin (2 mM)) supplemented with 5% heat inactivated fetal bovine serum (FBS) to give a single cell suspension of the spleen cell. After hemolysis treatment, the suspension was adjusted to $10^7$ cells/ml with RPMI1640 medium containing $10^{-4}$ M 2-mercaptoethanol and 10%/ FBS and used as a reaction cell suspension.

The reaction cell suspension (50 $\mu$l) prepared by the above method, stimulated cell suspension (50 $\mu$l) and the test compound (100 $\mu$l) prepared using RPMI1640 medium containing 10% FBS were added to a 96 well plate and incubated at 37° C. under 5% $CO_2$ gas, 95% air for 4 days.

A pigment assay using 3-(4,5-dimethylthiazol-2-yl)-2,5-diphenyltetrazolium bromide (MTT) was applied for the determination of lymphocyte transformation reaction.

After the completion of culture, the supernatant (100 $\mu$l) in each well was removed, and 5 mg/ml MTT solution (20 $\mu$l) was added to each well, which was followed by incubation at 37° C. for 4 hours. Then, a 0.01 N hydrochloric acid solution (100 $\mu$l) containing 10% sodium dodecyl sulfate was added and the mixture was incubated at 37° C. overnight. The resulting purple crystals of formazan was dissolved and absorbance at 550 nm was measured using a microplate absorption meter, which was used as the index of lymphocyte transformation reaction of the mouse allogenic MLR. The inhibition of mouse allogenic MLR was evaluated by calculating the inhibition percentage by the following formula. The results are shown in Table 7.

TABLE 7

$$\text{Inhibition (\%)} = \left(1 - \frac{\text{Absorbance of MLR with addition of test compound} - \text{absorbance of reacted cells alone}}{\text{Absorbance of MLR without addition of test compound} - \text{absorbance of reacted cells alone}}\right) \times 100$$

| Test compound | Bone resorption inhibition % ($\mu$M) | Mouse allogenic MLR inhibitory activity $IC_{50}$ ($\mu$M) |
|---|---|---|
| Compound 80.2HCl.H$_2$O | 40.9(100) | 9.6 |
| Compound 109.2HCl | 42.6(100) | 1.6 |
| Compound 112.2HCl | 75.7(100) | 4.4 |
| Compound 110.2HCl.H$_2$O | 74.0(100) | 1.1 |
| Compound 142.2HCl.H$_2$O | 44.2(100) | |
| Compound 143.2HCl.H$_2$O | 39.4(100) | |
| Compound 308.2HCl | | 13.9 |

Experimental Example 10: Inhibition of Cell Growth of SK-Mel-28 Melanoma

Human SK-Mel-28 melanoma ($10^4$ cells) and the test compound were suspended in RPMI1640 medium containing 100 µl of 10%/ FBS and incubated in a 96 well plate at 37° C. under 5% $CO_2$ gas for 72 hours. After the incubation, 10 µl of MTT (5 mg/ml) was added to each well and the cells were incubated at 37° C. under 5% $CO_2$ gas for 4 hours. Then, 10% sodium dodecyl sulfate and 0.01 N hydrochloric acid solution were each added by 10 µl to respective wells. After the plate was stood overnight, absorbance at 570 rim was measured using a microplate reader and the inhibition percentage (% cytotoxicity) was calculated by the following formula The results are shown in Table 8.

The cytotoxicity against human cultured tumor cells was confirmed by pigment method (Carmichael et al., Cancer Res., 47, 936–942, 1987 : Mosman, J. Immunol. Methods, 65, 55–63, 1983) using 3-(4,5-dimethylthiazol-2-yl)-2,5-diphenyltetrazolium bromide (MTT).

The test compound was dissolved in dimethyl sulfoxide and diluted with RPMI1640 medium before use. The final dimethyl sulfoxide concentration was adjusted to not more than 0.25%.

TABLE 8

$$\text{Inhibition} (\%) = \left(1 - \frac{\text{Absorbance when test compound was added}}{\text{Absorbance when test compound was not added}}\right) \times 100$$

| Test compound | Cell growth inhibition $IC_{50}$ (µM) |
|---|---|
| Compound 115.2HBr.1/4$H_2O$ | 9 |
| Compound 109.2HCl | 58 |
| Compound 142.2HCl.$H_2O$ | 59 |
| Compound 145.2HCl.$H_2O$ | 62 |

Experimental Example 11: Inhibition of Angiogenesis

The inhibition of angiogenesis was evaluated by using the inhibition of lumen formation in vascular endothelial cell as an index. To be specific, normal human umberical vascular endothelial cells (KURABO INDUSTRIES LTD.) were suspended in E-GMUV medium at $5.5 \times 10^4$ cells/ml and 400 µl therefrom was added on matrigel plate (EHS sarcoma-derived reconstructed basement membrane, Collaborative Biomedical Products). Then, the test compound (1 mM solution, 4 µl) was added and the cells were incubated at 37° C. under 5% $CO_2$ gas for 18 hours. After the completion of the incubation, the number of lumen per predetermined area was counted under a microscope. Inasmuch as the number of lumen increases by the inhibition of lumen formation, the test compound was evaluated by comparison of the number of lumen with the control. The results are shown in Table 9.

TABLE 9

| Test compound | Number of lumen (10 µM) |
|---|---|
| Compound 109.2HCl | 153% |
| Compound 80.2HCl.$H_2O$ | 174% |
| Compound 110.2HCl.$H_2O$ | 203% |
| Compound 165.2HCl.3/2$H_2O$ | 222% |
| Compound 204.2HCl | 133% |

Experimental Example 12: Inhibition of Growth of Vascular Smooth Muscle Cell

The separation from the artery of rat and culture of smooth muscle cell (SMO) followed the explant method of Ross (Ross, R. and Glomset, J. A., N. Engl. J. Med., 295, 369–420, 1976). Male wistar rats (10 week old) was slaughtered by cutting the carotid arteries and aorta of thorax was removed. After removal of fat tissues around the tunica extema and peeling of tunica intima, the artery was minced and incubated in 10% fetal bovine serum (FBS)-containing DMEM medium at 37° C. under 5% $CO_2$ gas. Seven days later, the out-grown cells were separated by trypsin treatment, washed with phosphate-buffered saline (PBS) and incubated in 10% FBS-containing DMEM medium in a 80 $cm^2$ culture kast The cells of subculture 2 were suspended in 10% FBS-containing DMEM medium at $5 \times 10^4$ cells/ml and 100 µl thereof per well was added to 96 well collagen-coated plate, which was incubated at 37° C. under 5% $CO_2$ gas for one day. The test compound was appropriately diluted with dimethyl sulfoxde (DMSO) and added to the 96 well plate. The concentration of DMSO in the medium was adjusted to 1%. After 48 hours, 10 µl of MTT solution (5 mg/ml) was added and, 4 hours later, 10% sodium dodecyl sulfate-0.01 N hydrochloric acid (50 µl) was added. The absorbance at 570 nm was measured the following day by an immuno-reader. The SMC growth inhibitory action of the test compound was shown by inhibition percentage calculated by the following formula The results are shown in Table 10.

TABLE 10

$$\text{Inhibition} (\%) = \left(1 - \frac{\text{Absorbance when test compound was added}}{\text{Absorbance when test compound was not added}}\right) \times 100$$

| Test compound | $IC_{50}$ (µM) |
|---|---|
| compound 153.2HCl | 27 |
| compound 157.2HCl.$H_2O$ | 55 |
| compound 165.2HCl.3/2$H_2O$ | 38 |
| compound 163.2HBr | 63 |

Experimental Example 13: Acute Toxicity

The compound 109.2HCl and compound 143.2HCl.$H_2O$ were respectively administered intraperitoneally to ddY mice and the mice were monitored for 5 days. As a result, the intraperitoneal administration at 30 mg/kg did not cause death.

The foregoing Formulation Examples and pharmacological experiments reveal that the compounds of the formula (I) and the formula (II) have strong Rho kinase inhibitory action. These Rho kinase inhibitors have vasodilating action, trachea relaxing action, peripheral blood flow increasing action, cell adhesion induction inhibitory action, tumor cell metastasis inhibitory action, bone resorption inhibitory action, mouse allogenic MLR inhibitory activity, tumor cell growth inhibitory action, angiogenesis inhibitory action, vascular smooth muscle cell growth inhibitory action and other various actions. Therefore, they are useful as pharmaceutical agents, particularly, a therapeutic agent of hypertension, a therapeutic agent of angina pectoris, a suppressive agent of cerebrovascular contraction, a therapeutic agent of asthma, a therapeutic agent of peripheral circulation disorder, a prophylactic agent of immature birth, a therapeutic agent of arteriosclerosis, an anti-cancer drug, an anti-inflammatory agent, an immunosuppressant, a therapeutic agent of autoimmune disease, an anti-AIDS drug, a contraceptive, a prophylactic agent of digestive tract infection, a therapeutic agent of osteoporosis, a therapeutic agent of retinopathy and a brain function improving drug.

In addition, since Rho kinase inhibitors of the present invention have strong Rho kinase inhibitory activity, they are also useful as reagents for the study relating to Rho and Rho kinase and as diagnostics of the diseases related to them.

This application is based on application No. 212409/1996 filed in Japan, the contents of which are incorporated hereinto by reference.

What is claimed is:

1. A method for inhibiting Rho kinase, comprising administering a pharmaceutically effective amount of a Rho kinase inhibitor to a patient in need thereof, wherein the Rho kinase inhibitor comprises an amide compound of the formula (I):

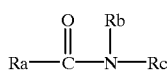

(I)

wherein

Ra is a group of the formula:

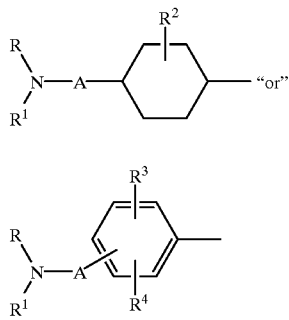

in the formulas (a) and (b),

R is hydrogen, alkyl or cycloalkyl, cycloaalkyl, phenyl or aracyl, which optionally have a substituent on the ring, or a group of the formula:

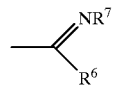

(d)

wherein $R^6$ is hydrogen, alkyl or formula: —$NR^8NR^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally having, in the ring, oxygen atom, sulfur atom or optionally substituted nitrogen atom, $R^1$ is hydrogen, alkyl or cycloalkyl, cycloalkylalkyl, phenyl or aralky, which optionally have a substituent on the ring, or R and $R^1$ in combination form, together with the adjacent nitrogen atom, a group forming a heterocycle optionally having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, alkylcarbamoyl or azide, and A is a group of the formula:

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, Rb is a hydrogen, an alkyl, an aralkyl, an aminoalkyl or a mono or dialkylaminoalkyl; and Rc is an optionally substituted pyridine, triazine, pyrimidine, pyrrolopyridine, pyrazolopyridine, pyrazolopyrimidine, 2,3-dihydropyrrolopyridine, imidazopyridine, pyrrolopyrimidine, imindazopyrimidine, pyrrolotriazine, pyrazolotriazine, triazolopyridine, triazolopyrimidine, or 2,3-dihydropyrrolopyrimidine, an isomer thereof and/or a pharmaceutically acceptable acid addition salt thereof.

2. The method according to claim 1, wherein the administration is for treatment of hypertension.

3. The method according to claim 1, wherein the administration is for treatment of angina pectoris.

4. The method according to claim 1, wherein the administration is for treatment of cerebrovascular contraction.

5. The method according to claim 1, wherein the administration is for treatment of asthma.

6. The method according to claim 1, wherein the administration is for treatment of peripheral circulation disorder.

7. The method according to claim 1, wherein the administration is for treatment of arteriosclerosis.

8. The method according to claim 1, wherein the administration is for treatment of cancer.

9. The method according to claim 1, wherein the administration is for treatment of an inflammation.

10. The method according to claim 1, wherein the administration is for treatment of an immune disease.

11. The method according to claim 1, wherein the administration is for treatment of an autoimmune disease.

12. The method according to claim 1, wherein the administration is for treatment of AIDS.

13. The method according to claim 1, wherein the administration is for treatment of osteoporosis.

14. The method according to claim 1, wherein the administration is for treatment of retinopathy.

15. The method according to claim 1, wherein the administration is for treatment of a brain function disorder.

16. The method according to claim 1, wherein the administration is for treatment of immature birth.

17. The method according to claim 1, wherein the administration is for fertilization and nidation of fertilized egg.

18. The method according to claim 1, wherein the administration is for treatment of digestive tract infection.

* * * * *